(12) United States Patent
Cherry et al.

(10) Patent No.: US 6,482,622 B1
(45) Date of Patent: Nov. 19, 2002

(54) AMYLOLYTIC ENZYME VARIANTS

(75) Inventors: Joel Robert Cherry, Davis, CA (US); Allan Svendsen, Birkerod (DK); Carsten Denmark Andersen, Vaerloese (DK); Lars Beier, Lyngby (DK); Torben Peter Frandsen, Frederiksberg C (DK); Thomas Schäfer, Farum (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/645,707

(22) Filed: Aug. 24, 2000

Related U.S. Application Data

(63) Continuation of application No. PCT/DK99/00087, filed on Feb. 26, 1999.
(60) Provisional application No. 60/077,509, filed on Mar. 11, 1998, and provisional application No. 60/077,795, filed on Mar. 12, 1998.

(30) Foreign Application Priority Data

| Feb. 27, 1998 | (DK) | 1998 00273 |
| Feb. 27, 1998 | (DK) | 1998 00269 |

(51) Int. Cl.⁷ ............................. C12N 9/00; C12N 1/10; C12N 9/24; C12N 9/28
(52) U.S. Cl. ...................... 435/193; 435/183; 435/200; 435/201; 435/202
(58) Field of Search ................. 435/183, 200, 435/201, 202, 193

(56) References Cited

U.S. PATENT DOCUMENTS 6,162,628 A * 12/2000 Cherry et al. ............ 435/202

FOREIGN PATENT DOCUMENTS

| EP | 0 120 693 B1 | 10/1984 |
| WO | WO 89/03421 | 4/1989 |
| WO | WO 91/04669 | 4/1991 |
| WO | WO 96/33267 | 10/1996 |

OTHER PUBLICATIONS

Alignment: Dk871.Dna, Empatent: E02907.
Diderichsen et al., FEMS Microbiology Letters 56 (1988) 53–60.
Nakamura et al., FEBS, vol. 296, No. 1, 37–40, 1992.
Nakamura et al. Biochemistry, 1994, 33, 9929–9936.
Japanese AN: 89–312221.
Wind et al., Eur. J. Biochem., vol. 253, p. 598–605 (1998).
Henrissat et al., Biochem. J., vol. 316, p. 695–696 (1996).
Christophersen et al., Starch/Stärke, vol. 50, p. 39–45 (1998).
Sin et al., Journal of Biotechnology, vol. 32 p. 283–288 (1994).
Kim et al., Biochemistry and Molecular Biology International, vol. 41, p. 227–234 (1997).
Penninga et al., Biochemistry, vol. 34, p. 3368–3376 (1995).
Norman et al., Depun Kagaku, vol. 39, p. 101–108 (1992).
Tachibana et al., Journal of Fermentation and Bioengineering, vol. 83, p. 540–548 (1997).
Birte Svensson, Plant Molecular Biology, vol. 25, p. 141–147 (1994).
Abstract of Demchuk et al., QSAR Mol. Modell., 9$^{th}$, p. 433–434 (1993).

* cited by examiner

*Primary Examiner*—Rebecca E. Prouty
*Assistant Examiner*—Manjunath N. Rao
(74) *Attorney, Agent, or Firm*—Elias Lambiris; Jason Garbell

(57) ABSTRACT

The inventors have discovered some striking, and not previously predicted structural similarities and differences between the structure of Novamyl and the reported structures of CGTases, and based on this they have constructed variants of maltogenic alpha-amylase having CGTase activity and variants of CGTase having maltogenic alpha-amylase activity. Further, on the basis of sequence homology between Novamyl® and CGTases, the inventors have constructed hybrid enzymes with one or more improvements to specific properties of the parent enzymes, using recombinant DNA methodology.

24 Claims, 5 Drawing Sheets

```
         10        20        30        40        50        60        70        80
---------SSSASVKGDVIYQIIIDRFYDGDTTNNPAKSYGLYDPTKSKWKMYWGGDLEGVRQKL----PYLKQLGVTTIWLS  72
ASDTAVSNVVNYSTDVIYQIVTDREVDGNTSNNPT----GDLYDPTHTSLKKYFGGDWQGIINKINDGYLTGMGVTAIWIS    77
APDTSVSNVVNYSTDVIYQIVTDRFLDGNPSNNPT----GDLYDPTHTSLKKYFGGDWQGIINKINDGYLTGMGITAIWIS    77
APDTSVSNKQNFSTDVIYQIFTDRFSDGNPANNPT----GAAFDGTCTNLRLYCGGDWQGIINKINDGYLTGMGVTAIWIS    77

PVLDNLDTLAGT-----DNTGYHGYWTRDFKQIEEHFGNWTTFDTLVNDAHQNGIKVIVDFVPNHSTPFKANDSTFAEGGA   148
QPVENIYAVLPDSTFGGSTSYHGYWARDFKKTNPYFGSFTDFQNLINTAHAHNIKVIIDFAPNHTSPASETDPTYAENGR    157
QPVENIYAVLPDSTFGGSTSYHGYWARDFKKTNPFFGSFTDFQNLIATAHAHNIKVIIDFAPNHTSPASETDPTYGENGR    157
QPVENIYSIINYSG-VNNTAYHGYWARDFKKTNPAYGTIADFQNLIAAAHAKNIKVIIDFAPNHTSPASSDQPSFAENGR    156

LYNNGTYMGNYFDDATKGYFHHNGDISNWDDRYEAQWKNFTDPAGFSLADLSQENGTIAQYLTDAAVQLVAHGADGLRID    228
LYDNGTLLGGYTNDT-NGYFHHYGGTD-FSSYEDGIYRNLF-----DLADLNQQNSTIDSYLKSAIKVWLDMGIDGIRLD    230
LYDNGVLLGGYTNDT-NGYFHHYGGTN-FSSYEDGIYRNLF-----DLADLDQQNSTIDSYLKAAIKLWLDMGIDGIRMD    230
LYDNGTLLGGYTNDT-QNLFHHNGGTD-FSTTENGIYKNLY-----DLADLNHNNSTVDVYLKDAIKMWLDLGIDGIRMD    229

AVKHFNSGFSKSLADKLYQKKDIFLVGEWYGDD-PGTANHLEKVRYANNSGVNVLDFDLNTVIRNVFGTFTQTMYDLNNM    307
AVKHMPFGWQKNFMDSILSYRPVFTFGEWFLG-TNEI--DVNNTYFANESGMSLLDFRFSQKVRQVFRDNTDTMYGLDSM    307
AVKHMAFGWQKNFMDSILSYRPVFTFGEWYLG-TNEV--DPNNTYFANESGMSLLDFRFAQKVRQVFRDNTDTMYGLDSM    307
AVKHMPFGWQKSFMAAVNNYKPVFTFGEWFLG-VNEV--SPENHKFANESGMSLLDFRFAQKVRQVFRDNTDNMYGLKAM    306

VNQTGNEYKYKENLITFIDNHDMSRFLSVNSNKANLHQALAFILTSRGTPSIYYGTEQYMAGGNDPYNRGMMPAFDTTTT    387
IQSTASDYNFINDMVTFIDNHDMDRFYN-GGSTRPVEQALAFTLTSRGVPAIYYGTEQYMTGNGDPYNRAMMTSFNTSTT    386
IQSTAADYNFINDMVTFIDNHDMDRFYT-GGSTRPVEQALAFTLTSRGVPAIYYGTEQYMTGNGDPYNRAMMTSFDTTTT    386
LEGSAADYAQVDDQVTFIDNHDMERFHASNANRRKLEQALAFTLTSRGVPAIYYGTEQYMSGGTDPDNRARIPSFSTSTT    386
```

FIG. 4A

```
AFKEVSTLAGLRRNNAAIQYGTTTQRWINNDVYIYERKFFNDVVLVAINRNTQSSYSISGLQTALPNGSYADYLSGLLGG   467
AYNVIKKLAPLRKSNPAIAYGTTQQRWINNDVYIYERKFGNNVALVAINRNLSTSYNITGLYTALPAGTYTDVLGGLLNG   466
AYNVIKKLAPLRKSNPAIAYGTQKQRWINNDVYIYERQFGNNVALVAINRNLSTSYYITGLYTALPAGTYSDMLGGLLNG   466
AYQVIQKLAPLRKCNPAIAYGSTQERWINNDVLIYERKFGSNVAVVAVNRNLNAPASISGLVTSLPQGSYNDVLGGLLNG   466
NGISVS-NGSVASFTLAPGAVSVWQYST-SASAPQIGSVAPNMGIPGNVVTIDGKGFGTTQGTVTFGGVTAT---VKSWT   543
NSISVASDGSVTPFTLSAGEVAVWQYVSSSN-SPLIGHVGPTMTKAGQTITIDGRGFGTTSGQVLFGSTAGT---IVSWD   542
SSITVSSNGSVTPFTLAPGEVAVWQYVSTTN-PPLIGHVGPTMTKAGQTITIDGRGFGTTAGQVLFGTTPAT---IVSWE   542
NTLSVGSGGAASNFTLAAGGTAVWQYTAATA-TPTIGHVGPMMAKPGVTITIDGRGFGSSKGTVYFGTTAVSGADITSWE   545

SNRIEVYVPNMAAGLTDVKVTA-GGVSSNLYS-YNILSGTQTSVVFTVKSAPPTNLGDKIYLTGNIPELGNWSTDTSGAV   620
DTEVKVKVPSVTPGKYNISLKTSSGATSNTYNININILTGNQICVRFVVNNASTVY-GENVYLTGNVAELGNWDTS----   616
DTEVKVKVPALTPGKYNITLKTASGVTSNSYNNINVLTGNQVCVRFVVNNATTVW-GENVYLTGNVAELGNWDTS----   616
DTQIKVKIPAVAGGNYNIKVANAAGTASNVYDNFEVLSGDQVSVRFVVNNATTAL-GQNVYLTGSVSELGNWDPA----   619

NNAQGPLLAP---NYPDWFYVFSVPAGKTIQFKFFIKRADGT-IQWENGSNHVATTPTGATGNITVTWQN   686
-KAIGPMFNQVVYQYPTWYDVSVPAGTTIQFKFIQFKFIKKN--GNTITWEGGSNHTYTVPSSSTGTIVNWQQ   683
-KAIGPMFNQVVYQYPTWYDVSVPAGTTIEFKFIKKN---GSTVTWEGGYNHVYTTPTSGTATVIVDWQP   683
-KAIGPMYNQVVYQYPNWYYDVSVPAGKTIEFKFLKKQ--GSTVTWEGGSNHTFTAPSSGTATINVNWQP   686
```

FIG. 4B

AMYLOLYTIC ENZYME VARIANTS

CROSS-REFERENCE TO RELATED APPLICATIONS

This application is a continuation of PCT/DK/99/00087 filed on Feb. 26, 1999, and claims priority under 35 U.S.C. 119 of Danish application nos. PA 1998 00269 and PA 1998 00273, both filed on Feb. 27, 1998, and U.S. provisional application Nos. 60/077,509 and 60/077,795, filed on Mar. 11, 1998 and Mar. 12, 1998, respectively, the contents of which are fully incorporated herein by reference.

FIELD OF THE INVENTION

The present invention relates to methods of converting a maltogenic alpha-amylase into a cyclodextrin glucanotransferase (CGTase) or vice versa or creating hybrids of the two. The invention also relates to the variants made by the methods.

BACKGROUND OF THE INVENTION

Cyclodextrin glucanotransferase (CGTase, EC 2.4.1.19) and maltogenic alpha-amylase (EC 3.2.1.133) are two classes of glycosylases that degrade starch by hydrolysis of the α-(1,4)-glycosidic bonds, but the initial products are predominantly cyclic for CGTases and linear for the maltogenic alpha-amylase.

Cyclomaltodextrin glucanotransferase (E.C. 2.4.1.19), also designated cyclodextrin glucanotransferase or cyclodextrin glycosyltransferase, abbreviated herein as CGTase, catalyses the conversion of starch and similar substrates into cyclomaltodextrins via an intramolecular transglycosylation reaction, thereby forming cyclomaltodextrins (or CD) of various sizes. Commercially most important are cyclodextrins of 6, 7 and 8 glucose units, termed α-, β- and γ-cyclodextrins, respectively.

CGTases are widely distributed and from several different bacterial sources, including Bacillus, Brevibacterium, Clostridium, Corynebacterium, Klebsiella, Micrococcus, Thermoanaerobacter and Thermoanaerobacterium have been extensively described in the literature. A CGTase produced by Thermoanaerobacter sp. has been reported in Norman B E, Jørgensen S T; *Denpun Kagaku* 1992 39 99–106, and WO 89/03421, and the amino acid sequence has been disclosed in WO 96/33267. The sequence of CGTases from *Thermoanaerobacterium thermosulfurigenes* and from *Bacillus circulansis* available on the Internet (SCOP or PDF home pages) as pdf file 1CIU, and the sequence of a CGTase from *B. circulans* is available as pdf file 1CDG.

Tachibana, Y., Journal of Fermentation and Bioengineering, 83 (6), 540–548 (1997) describes the cloning and expression of a CGTase. Variants of CGTases have been described by Kim, Y. H., Biochemistry and Molecular Biology International, 41 (2), 227–234 (1997); Sin K-A, Journal of Biotechnology, 32 (3), 283–288 (1994); D Penninga, Biochemistry, 34 (10), 3368–3376 (1995); and WO 96/33267.

Maltogenic alpha-amylase (glucan 1,4-a-maltohydrolase, E.C. 3.2.1.133) is able to hydrolyze amylose and amylopectin to maltose in the alpha-configuration, and is also able to hydrolyze maltotriose as well as cyclodextrin.

A maltogenic alpha-amylase from Bacillus (EP 120 693) is commercially available under the trade name Novamyl® (product of Novo Nordisk A/S, Denmark) and is widely used in the baking industry as an anti-staling agent due to its ability to reduce retrogradation of starch (WO 91/04669).

The maltogenic alpha-amylase Novamyl® shares several characteristics with cyclodextrin glucanotransferases (CGTases), including sequence homology (Henrissat B, Bairoch A; Biochem. J., 316, 695–696 (1996)) and formation of transglycosylation products (Christophersen, C., et al., 1997, Starch, vol. 50, No. 1, 39–45).

BRIEF DESCRIPTION OF THE INVENTION

The inventors have discovered some striking, and not previously predicted structural similarities and differences between the structure of Novamyl and the reported structures of CGTases, and based on this they have constructed variants of maltogenic alpha-amylase having CGTase activity and variants of CGTase having maltogenic alpha-amylase activity. Further, on the basis of sequence homology between Novamyl® and CGTases, the inventors have constructed hybrid enzymes with one or more improvements to specific properties of the parent enzymes, using recombinant DNA methodology.

Accordingly, the present invention provides a polypeptide which:

a) has at least 70% identity to amino acids 1–686 of SEQ ID NO: 1;

b) comprises an amino acid modification which is an insertion, substitution or deletion compared to SEQ ID NO: 1 in a region corresponding to amino acids 40–43, 78–85, 136–139, 173–180, 188–195 or 259–268; and c) has the ability to form cyclodextrin when acting on starch.

The invention also provides a polypeptide which:

a) has an amino acid sequence having at least 70% identity to a parent cyclodextrin glucanotransferase (CGTase);

b) comprises an amino acid modification which is an insertion, substitution or deletion compared to the parent CGTase in a region corresponding to amino acids 40–43, 78–85, 136–139, 173–180, 188–195 or 259–268 of SEQ ID NO: 1; and c) has the ability to form linear oligosaccharides when acting on starch.

Further, the invention provides a method for constructing a maltogenic alpha-amylase, comprising:

a) recombining DNA encoding a cyclodextrin glucanotransferase (CGTase) and DNA encoding a maltogenic alpha-amylase;

b) using the recombinant DNA to express a polypeptide; and c) testing the polypeptide to select a polypeptide having the ability to form linear oligosaccharides when acting on starch.

Finally, the invention provides a method of selecting DNA encoding maltogenic alpha-amylase in a DNA pool, comprising:

a) amplifying DNA encoding maltogenic alpha-amylase by a polymerase chain reaction (PCR) using primers encoding a partial amino acid sequence of amino acids 1–686 of SEQ ID NO: 1, preferably comprising at least 5 amino acid residues, preferably comprising one or more of positions 188–196, more preferably comprising positions 190–194, b) cloning and expressing the amplified DNA, and c) screening for maltogenic alpha-amylase activity.

BRIEF DESCRIPTION OF THE DRAWINGS

FIGS. 4 and 5 show an alignment of the amino acid sequence of Novamyl (1–686 of SEQ ID NO: 1) with the sequence of 3 CGTases as described below.

DETAILED DESCRIPTION OF THE INVENTION

Maltogenic Alpha-amylase

Figure 1:
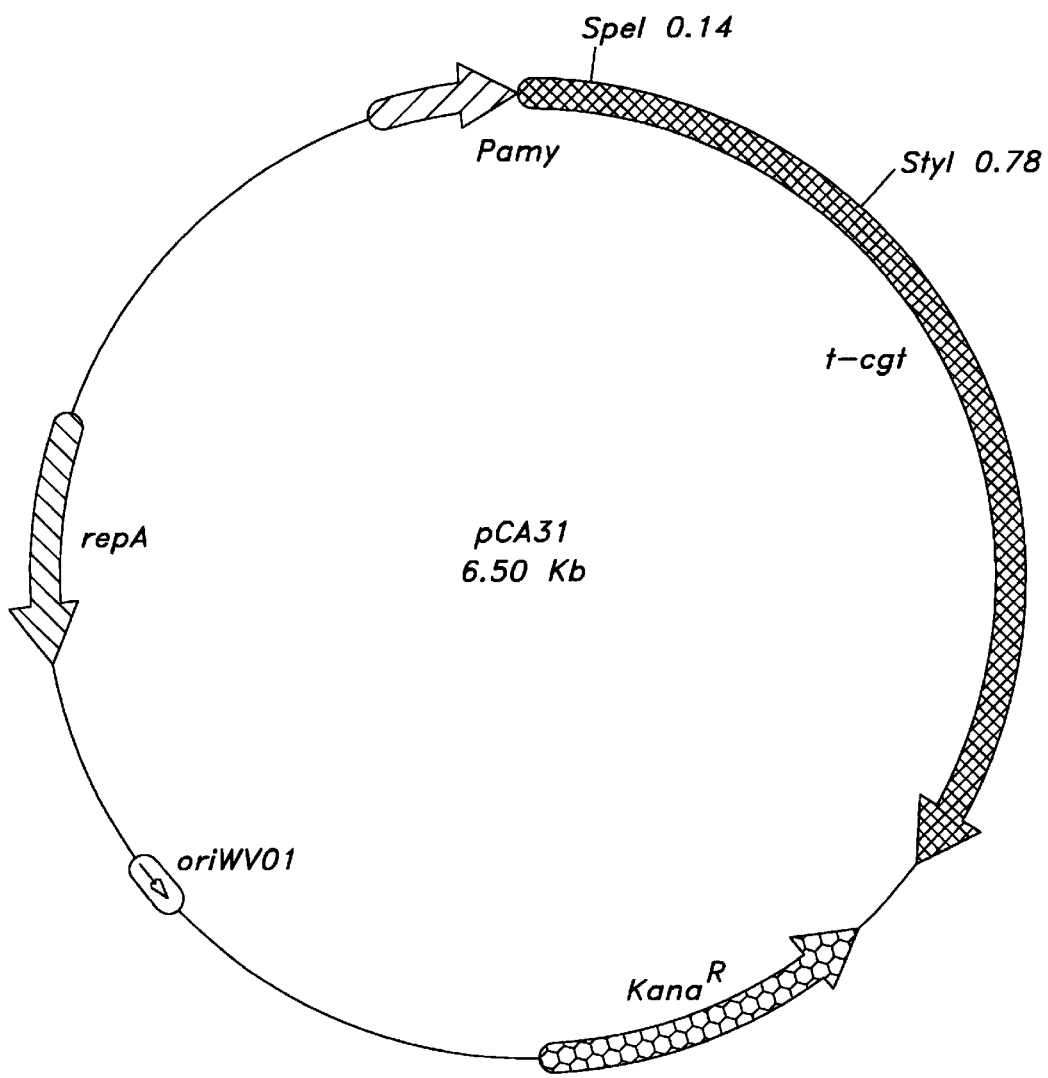
FIG. 1 shows plasmid pCA31, described in Example 1.

The parent maltogenic alpha-amylase used in the invention is an enzyme classified in EC 3.2.1.133. The enzymatic activity does not require a non-reducing end on the substrate and the primary enzymatic activity results in the degradation of amylopectin and amylose to maltose and longer maltodextrins. It is able to hydrolyze amylose and amylopectin to maltose in the alpha-configuration, and is also able to hydrolyze maltotriose as well as cyclodextrin.

A particularly preferred maltogenic alpha-amylase is the amylase cloned from Bacillus as described in EP 120 693 (hereinafter referred to as Novamyl). Novamyl has the amino acid sequence set forth in amino acids 1–686 of SEQ ID NO: 1. Novamyl is encoded in the gene harbored in the Bacillus strain NCIB 11837 which has the nucleic acid sequence set forth in SEQ ID NO:1.

CGTase

The parent CGTase used in the invention is an enzyme classified in EC 2.4.1.19. It may be from any source, e.g. bacterial sources, including Bacillus, Brevibacterium, Clostridium, Corynebacterium, Klebsiella, Micrococcus, Thermoanaerobacter and Thermoanaerobacterium.

The CGTase preferably has one or more of the following characteristics:

i) an amino acid sequence having at least 50% identity to amino acids 1–686 of SEQ ID NO: 1, preferably at least 60%;

ii) being encoded by a DNA sequence which hybridizes at conditions described below to the DNA sequence set forth in SEQ ID NO:1 or to the DNA sequence encoding Novamyl harbored in the Bacillus strain NCIB 11837; and iii) a catalytic binding site comprising amino acid residues corresponding to D228, E256 and D329 as shown in the amino acid sequence set forth in amino acids 1–686 of SEQ ID NO: 1.

Variants of CGTase

The CGTase variant of this invention has the ability to form linear oligosaccharides when acting on starch. The starch hydrolysis and the analysis of initial reaction products may be carried out as described in an Example.

The CGTase variant has a modification of at least one amino acid residue in a region corresponding to residues 40–43, 78–85, 136–139, 173–180, 189–195 or 259–268 of SEQ ID NO: 1. Each modification may be an insertion, a deletion or a substitution, of one or more amino acid residues in the region indicated. The modification of the parent CGTase is preferably such that the resulting modified amino acid or amino acid sequence more closely resembles the corresponding amino acid or structural region in Novamyl. Thus, the modification may be an insertion of or a substitution with an amino acid present at the corresponding position of Novamyl, or a deletion of an amino acid not present at the corresponding position of Novamyl.

The CGTase variant may particularly comprise an insertion into a position corresponding to the region D190-F194 of Novamyl (amino acid sequence shown in SEQ ID NO: 1). The insertion may comprise 3–7 amino acids, particularly 4–6, e.g. 5 amino acids. The insertion may be DPAGF (SEQ ID NO: 27) as found in Novamyl or an analogue thereof, e.g. with the first amino acid being negative, the last one being aromatic, and the ones in between being preferably P, A or G. The variant may further comprise a substitution at the position corresponding to T189 of Novamyl with a neutral amino acid which is less bulky than F, Y or W. Other examples of insertions are DAGF (SEQ ID NO: 28) DPGF, (SEQ ID NO: 28) DPF, DPAAGF, (SEQ ID NO: 30) and DPAAGGF (SEQ ID NO: 31).

Modifications in the region 78–85 preferably include deletion of 2–5 amino acids, e.g. 3 or 4. Preferably, any aromatic amino acid in the region 83–85 should be deleted or substituted with a non-aromatic.

Modifications in the region 259–268 preferably include deletion of 1–3 amino acid, e.g. two. The region may be modified so as to correspond to Novamyl The CGTase variant may comprise further modifications in other regions, e.g. regions corresponding to amino acids 37–39, 44–45, 135, 140–145, 181–186, 269–273, or 377–383 of Novamyl.

Additional modifications of the amino acid sequence may be modeled on a second CGTase, i.e. an insertion of or substitution with an amino acid found at a given position in the second CGTase, or they may be made close to the substrate (less than 8 Å from the substrate, e.g. less than 5 Å or less than 3 Å) as described in WO 96/33267.

The following are some examples of variants based on a parent CGTase from Thermoanaerobacter (using *B. circulans* numbering). Similar variants may be made from other CGTases.

L194F+*194aT+*194bD+*194cP+*194dA+*194eG+D196S

L87H+D89*+T91G+F91aY+G92*+G93*+S94*+L194F+*194aT+*194bD+*194cP+*194dA+*194eG+D196S

*194aT+*194bD+*194cP+*194dA+*194eG+D196S

L87H+D89*+T91G+F91aY+G92*+G93*+S94*+*194aT+*194bD+*194cP+*194dA+*194eG+D196S

Y260F+L261 G+G262D+T263D+N264P+E265G+V266T+*266aA+*266bN+D267H+P268V

*194aT+*194bD+*194cP+*194dA+*194eG+D196S+Y260F+L261G+G262D+T263D+N264P+E265G+V266T+*266aA+*266bN+D267H+P268V

Variants of Novamyl

The Novamyl variant of this invention has the ability to form cyclodextrin when acting on starch. The starch hydrolysis and the analysis of reaction products may be carried out as described in an Example.

The Novamyl variant has a modification of at least one amino acid residue in the same regions described above for CGTase variants. However, the modifications are preferably in the opposite direction, i.e. such that the resulting modified amino acid or amino acid sequence more closely resembles the corresponding amino acid or structural region of a CGTase. Thus, the modification may be an insertion of or a substitution with an amino acid present at the corresponding position of a CGTase, or a deletion of an amino acid not present at the corresponding position of a CGTase.

Preferred modifications include a deletion in the region 190–195, preferably the deletion Δ (191–195) and/or a substitution of amino acid 188 and/or 189, preferably F188L and/or Y189Y.

Amino Acid Identity

For purposes of the present invention, the degree of identity may be suitably determined according to the method described in Needleman, S. B. and Wunsch, C. D., (1970), Journal of Molecular Biology, 48, 443–45, with the following settings for polypeptide sequence comparison: GAP creation penalty of 3.0 and GAP extension penalty of 0.1. The determination may be done by means of a computer program known such as GAP provided in the GCG program package (Program Manual for the Wisconsin Package, Version 8, August 1994, Genetics Computer Group, 575 Science Drive, Madison, Wis., USA 53711).

The variants of the invention have an amino acid identity with the parent enzyme (Novamyl or CGTase) of at least 70%, preferably at least 80%, e.g. at least 90%, particularly at least 95% or at least 98%.

Hybridization

The hybridization referred to above indicates that the analogous DNA sequence hybridizes to the nucleotide probe corresponding to the protein encoding part of the nucleic sequence shown in SEQ ID NO:1, under at least low stringency conditions as described in detail below.

Suitable experimental conditions for determining hybridization at low stringency between a nucleotide probe and a homologous DNA or RNA sequence involves presoaking of the filter containing the DNA fragments or RNA to hybridize in 5×SSC (sodium chloride/sodium citrate, Sambrook, J., Fritsch, E. J., and Maniatis, T. (1989) *Molecular cloning: a laboratory manual,* Cold Spring Harbor Laboratory Press, New York) for 10 min, and prehybridization of the filter in a solution of 5×SSC, 5×Denhardt's solution (Sambrook, et al., op.cit), 0.5% SDS and 100 µg/ml of denatured sonicated salmon sperm DNA (Sambrook, et al., op.cit.), followed by hybridization in the same solution containing a random-primed (Feinberg, A. P. and Vogelstein, B. (1983) *Anal. Biochem.* 132:6–13), $^{32}$P-dCTP-labeled (specific activity>1×10$^9$ cpm/µg) probe for 12 hours at ca. 45° C. The filter is then washed twice for 30 minutes in 2×SSC, 0.5% SDS at least 55° C. (low stringency), more preferably at least 60° C. (medium stringency), more preferably at least 65° C. (medium/high stringency), more preferably at least 70° C. (high stringency), even more preferably at least 75° C. (very high stringency).

Molecules which hybridize to the oligonucleotide probe under these conditions are detected by exposure to x-ray film.

Corresponding Amino Acids

Corresponding amino acids for the following 4 amino acid sequences are shown in the alignment in FIGS. 4a–4b which is based on the three-dimensional structure of the sequences.

1) Novamyl (amino acids 1–686 of SEQ ID NO: 1)
2) CGTase from *Thermoanaerobacterium thermosulfurigenes* (pdf file 1 CIU)
3) CGTase from Thermoanaerobacter, described in WO 96/33267
4) CGTase from *Bacillus circulans* (pdf file I CDG)

Corresponding amino acid residues in other CGTases may be found by aligning with one of the sequences in FIGS. 4a–4b by to the method described in Needleman (supra) using the same parameters, e.g. by means of the GAP program (supra).

Nomenclature for Amino Acid Modifications

The nomenclature used herein for defining mutations is essentially as described in WO 92/05249. Thus, F188L indicates a substitution of the amino acid F (Phe) in position 188 with the amino acid L (Leu). Δ (191–195) or Δ (191–195) indicates a deletion of amino acids in positions 191–195. 192-A-193 indicates an insertion of A between amino acids 192 and 193. *194aT indicates an insertion of T at the first position after 194. G92* indicates a deletion of G at position 92.

Recombination of CGTase and Maltogenic Alpha-amylase

The present invention further relates to a method for constructing a variant enzyme comprising Novamyl and one or more parent CGTases, wherein said variant has at least one altered property relative to Novamyl and said parent CGTases, which method comprises:

i) generating DNA fragments encoding amino acid sequences obtainable from Novamyl and said parent CGTases;

ii) constructing a hybrid variant which contains amino acid sequences generated in step i) by in vivo or in vitro DNA shuffling; and iii) testing the resulting variant for said property.

The methods for generating DNA fragments referred to in step i) of the method above are well known in the art and may include, for example, treatment of a DNA sequence encoding an amino acid sequence with a restriction enzyme, e.g., DNAse I.

The DNA shuffling referred to in step ii) in the method above may be recombination, either in vivo or in vitro, of nucleotide sequence fragment(s) between two or more polynucleotides resulting in output polynucleotides (i.e., polynucleotides having been subjected to a shuffling cycle) having a number of nucleotide fragments exchanged, in comparison to the input polynucleotides (i.e. starting point polynucleotides). Shuffling may be accomplished either in vitro or in vivo by recombination within a cell by methods described in the art (cf., Crameri, et al, 1997, Nature Biotechnology Vol. 15:436–438).

In a preferred embodiment, at least one DNA fragment obtainable from Novamyl in step i) of the method above encodes an amino acid sequence, which is determined to be of relevance for altering said property.

In a more preferred embodiment, a hybrid variant of a parent CGTase is obtained by the above method comprising a modification of at least one amino acid residue in the group consisting of amino acid residues corresponding to residues 37 to 45, residues 135 to 145, residues 173 to 180, residues 189 to 196, residues 261 to 266, residues 327 to 330, and residues 370 to 376 of SEQ ID NO: 1.

In another more preferred embodiment, a hybrid variant comprising Novamyl and one or more parent CGTases is constructed by the above method in which the amino acid sequence of Asp190-Pro191-Ala192-Gly-193-Phe194 corresponding to the positions in the amino acid sequence shown in SEQ ID NO: 1 is inserted into the corresponding positions in said hybrid, wherein the corresponding positions is determined on the basis of amino acid sequence alignment.

In another more preferred embodiment, a hybrid variant comprising Novamyl and one or more parent CGTase is obtained by the above method in which the amino acid sequence of Asp190-Pro191-Ala192-Gly193-Phe194-Ser95 corresponding to the positions in the amino acid sequence shown in SEQ ID NO: 1 is inserted into the corresponding positions in said hybrid, wherein the corresponding positions is determined on the basis of amino acid sequence alignment.

It is possible to use the unique active site loop to select hybrid enzymes with maltogenic alpha-amylase activity from a library of random recombinants. Thus, a maltogenic alpha-amylase and a CGTase may be randomly recombined, e.g. by the DNA shuffling method of Crameri A, et al., op.cit. Those resulting mutants containing the Novamyl loop may be selected using PCR, e.g. as described above in the Examples.

The property to be altered may be substrate specificity, substrate binding, substrate cleavage pattern, specific activity of cleavage, transglycosylation, and relative activity of cyclization.

The DNA sequence encoding a parent CGTase to be used in the methods of the invention may be isolated from any cell or microorganism producing the CGTase in question using methods known in the art.

Cloning a DNA Sequence Encoding a CGTaseCloning a DNA Sequence Encoding an a-amylaseCloning a DNA Sequence Encoding an a-amylase The DNA sequence encoding a parent CGTase may be isolated from any cell or microorganism producing the CGTase in question, using various methods well known in the art, for example, from the Bacillus strain NCIB 11837.

First, a genomic DNA and/or cDNA library should be constructed using chromosomal DNA or messenger RNA from the organism that produces the CGTase to be studied. Then, if the amino acid sequence of the CGTase is known, homologous, labeled oligonucleotide probes may be synthesized and used to identify CGTase-encoding clones from a genomic library prepared from the organism in question. Alternatively, a labeled oligonucleotide probe containing sequences homologous to a known CGTase gene could be used as a probe to identify CGTase-encoding clones, using hybridization and washing conditions of lower stringency.

Another method for identifying CGTase-encoding clones involves inserting fragments of genomic DNA into an expression vector, such as a plasmid, transforming maltogenic alpha-amylase negative bacteria with the resulting genomic DNA library, and then plating the transformed bacteria onto agar containing a substrate for maltogenic alpha-amylase, thereby allowing clones expressing maltogenic alpha-amylase activity to be identified.

Alternatively, the DNA sequence encoding the enzyme may be prepared synthetically by established standard methods, e.g. the phosphoroamidite method described by S. L. Beaucage and M. H. Caruthers (1981) or the method described by Matthes et al. (1984). In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin, wherein the fragments correspond to various parts of the entire DNA sequence, in accordance with techniques well known in the art. The DNA sequence may also be prepared by polymerase chain reaction (PCR) using specific primers, for instance as described in U.S. Pat. No. 4,683,202 or R. K. Saiki et al. (1988).

Random Mutagenesis

A general approach for modifying proteins and enzymes has been based on random mutagenesis, for instance, as disclosed in U.S. Pat. No. 4,894,331 and WO 93/01285. For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the maltogenic alpha-amylase enzyme by any published technique, using e.g. PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program (cf., Tomandl, D. et al., 1997, Journal of Computer-Aided Molecular Design 11:29–38; Jensen, L J, Andersen, K V, Svendsen, A, and Kretzschmar, T (1998) Nucleic Acids Research 26:697–702) which, inter alia, ensures that introduction of stop codons is avoided.

When PCR-generated mutagenesis is used, either a chemically treated or non-treated gene encoding a parent CGTase enzyme is subjected to PCR under conditions that increase the misincorporation of nucleotides (Deshler 1992; Leung et al., Technique, Vol.1,1989, pp.11–15).

A mutator strain of E. coli (Fowler et al., Molec. Gen. Genet., 133, 1974, pp. 179–191), S. cereviseae or any other microbial organism may be used for the random mutagenesis of the DNA encoding the CGTase by, e.g., transforming a plasmid containing the parent CGTase into the mutator strain, growing the mutator strain with the plasmid and isolating the mutated plasmid from the mutator strain. The mutated plasmid may be subsequently transformed into the expression organism.

The DNA sequence to be mutagenized may be conveniently present in a genomic or cDNA library prepared from an organism expressing the parent CGTase. Alternatively, the DNA sequence may be present on a suitable vector such as a plasmid or a bacteriophage, which as such may be incubated with or otherwise exposed to the mutagenising agent. The DNA to be mutagenized may also be present in a host cell either by being integrated in the genome of said cell or by being present on a vector harbored in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to expression or screening. Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans or Streptomyces murinus; and gram negative bacteria such as E. coli.

The mutated DNA sequence may further comprise a DNA sequence encoding functions permitting expression of the mutated DNA sequence.

DNA Shuffling

Alternative methods for rapid preparation of modified polypeptides may be prepared using methods of in vivo or in vitro DNA shuffling wherein DNA shuffling is defined as recombination, either in vivo or in vitro, of nucleotide sequence fragment(s) between two or more polynucleotides resulting in output polynucleotides (i.e., polynucleotides having been subjected to a shuffling cycle) having a number of nucleotide fragments exchanged, in comparison to the input polynucleotides (i.e. starting point polynucleotides). Shuffling may be accomplished either in vitro or in vivo by recombination within a cell by methods described in the art.

For instance, Weber et al. (1983, Nucleic Acids Research, vol. 11, 5661–5661) describe a method for modifying genes by in vivo recombination between two homologous genes, wherein recombinants were identified and isolated using a resistance marker.

Pompon et al., (1989, Gene 83:15–24) describe a method for shuffling gene domains of mammalian cytochrome P-450 by in vivo recombination of partially homologous sequences in Saccharomyces cereviseae by transforming Saccharomyces cereviseae with a linearized plasmid with filled-in ends, and a DNA fragment being partially homologous to the ends of said plasmid.

In WO 97/07205 a method is described whereby polypeptide variants are prepared by shuffling different nucleotide sequences of homologous DNA sequences by in vivo recombination using plasmid DNA as template.

U.S. Pat. No. 5,093,257 (Genencor Int. Inc.) discloses a method for producing hybrid polypeptides by in vivo recombination. Hybrid DNA sequences are produced by forming a circular vector comprising a replication sequence, a first DNA sequence encoding the amino-terminal portion of the hybrid polypeptide, a second DNA sequence encoding the carboxy-terminal portion of said hybrid polypeptide. The circular vector is transformed into a rec positive microorganism in which the circular vector is amplified. This results in recombination of said circular vector mediated by the naturally occurring recombination mechanism of the rec positive microorganism, which include prokaryotes such as Bacillus and E. coli, and eukaryotes such as Saccharomyces cereviseae.

One method for the shuffling of homologous DNA sequences has been described by Stemmer (Stemmer, (1994), Proc. Natl. Acad. Sci. USA, Vol. 91, 10747–10751; Stemmer, (1994), Nature, vol. 370, 389–391; Crameri A, Dawes G, Rodriguez E Jr, Silver S, Stemmer WPC (1997) Nature Biotechnology Vol. 15, No. 5 pp. 436–438). The method concerns shuffling homologous DNA sequences by using in vitro PCR techniques. Positive recombinant genes containing shuffled DNA sequences are selected from a DNA library based on the improved function of the expressed proteins.

The above method is also described in WO 95/22625 in relation to a method for shuffling homologous DNA sequences. An important step in the method described in WO 95/22625 is to cleave the homologous template double-stranded polynucleotide into random fragments of a desired size followed by homologously reassembling of the fragments into full-length genes.

Site-directed Mutagenesis

Once a maltogenic alpha-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the maltogenic alpha-amylase-encoding sequence, is created in a vector carrying the maltogenic alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method because a multitude of oligonucleotides, of various lengths, can be introduced.

Another method of introducing mutations into a maltogenic alpha-amylase-encoding DNA sequences is described in Nelson and Long, Analytical Biochemistry 180, 1989, pp. 147–151. It involves a 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Localized Random Mutagenesis

The random mutagenesis may be advantageously localised to a part of the parent CGTase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Expression of Maltogenic Alpha-amylase Variants

The construction of the variant of interest is accomplished by cultivating a microorganism comprising a DNA sequence encoding the variant under conditions which are conducive for producing the variant, and optionally subsequently recovering the variant from the resulting culture broth. This is described in detail further below.

According to the invention, a DNA sequence encoding the variant produced by methods described above, or by any alternative methods known in the art, can be expressed, in the form of a protein or polypeptide, using an expression vector which typically includes control sequences encoding a promoter, operator, ribosome binding site, translation initiation signal, and, optionally, a repressor gene or various activator genes.

The recombinant expression vector carrying the DNA sequence encoding an maltogenic alpha-amylase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a maltogenic alpha-amylase variant of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes, etc. For transcription in a fungal host, examples of useful promoters are those derived from the gene encoding A. oryzae TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the maltogenic alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracycline resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

While intracellular expression may be advantageous in some respects, e.g. when using certain bacteria as host cells, it is generally preferred that the expression is extracellular. In general, the Bacillus α-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding maltogenic alpha-amylase variant, the promoter, terminator and other elements, respectively, and to insert them into suitable vectors containing the information necessary for replication, are well known to persons skilled in the art (cf., for instance, Sambroo, et al., op.cit.).

The cell of the invention, either comprising a DNA construct or an expression vector of the invention as defined above, is advantageously used as a host cell in the recombinant production of a maltogenic alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gram negative bacteria such as *E. coli.* The transformation of the bacteria may, for instance, be effected by protoplast transformation or by using competent cells in a manner known per se.

The yeast organism may favorably be selected from a species of Saccharomyces or Schizosaccharomyces, e.g. *Saccharomyces cereviseae.* The filamentous fungus may advantageously belong to a species of Aspergillus, e.g. *Aspergillus oryzae* or *Aspergillus niger.* Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing a maltogenic alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the maltogenic alpha-amylase variant of the invention. Suitable media are available from commercial suppliers or may be prepared according to published recipes (e.g. as described in catalogues of the American Type Culture Collection).

The maltogenic alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

Screening of Variants with Maltogenic Alpha-amylase Activity

Variants produced by any of the methods described above may be tested, either prior to or after purification, for maltogenic alpha-amylase activity, such as amylolytic activity, in a screening assay which measures the ability of the variant to degrade starch. The screening in step 10 in the above-mentioned random mutagenesis method of the invention may be conveniently performed by use of a filter assay based on the following procedure: A microorganism capable of expressing the variant of interest is incubated on a suitable medium and under suitable conditions for secretion of the variant, the medium being covered with two filters comprising a protein-binding filter placed under a second filter exhibiting a low protein binding capability. The microorganism is grown on the second, top filter. Subsequent to the incubation, the bottom protein-binding filter comprising enzymes secreted from the microorganism is separated from the second filter comprising the microorganism. The protein-binding filter is then subjected to screening for the desired enzymatic activity, and the corresponding microbial colonies present on the second filter are identified. The first filter used for binding the enzymatic activity may be any protein-binding filter, e.g., nylon or nitrocellulose. The second filter carrying the colonies of the expression organism may be any filter that has no or low affinity for binding proteins, e.g., cellulose acetate or Durapore™.

Screening consists of treating the first filter to which the secreted protein is bound with a substrate that allows detection of the amylolytic activity. The enzymatic activity may be detected by a dye, fluorescence, precipitation, pH indicator, IR-absorbance or any other known technique for detection of enzymatic activity. The detecting compound may be immobilized by any immobilizing agent e.g. agarose, agar, gelatine, polyacrylamide, starch, filter paper, cloth; or any combination of immobilizing agents. For example, amylolytic activity can be detected by Cibacron Red labeled amylopectin, which is immobilized in agarose. Amylolytic activity on this substrate produces zones on the plate with reduced red color intensity.

To screen for variants with increased stability, the filter with bound maltogenic alpha-amylase variants can be pretreated prior to the detection step described above to inactivate variants that do not have improved stability relative to the parent CGTase. This inactivation step may consist of, but is not limited to, incubation at elevated temperatures in the presence of a buffered solution at any pH from pH 2 to 12, and/or in a buffer containing another compound known or thought to contribute to altered stability e.g., surfactants, EDTA, EGTA, wheat flour components, or any other relevant additives. Filters so treated for a specified time are then rinsed briefly in deionized water and placed on plates for activity detection as described above. The conditions are chosen such that stabilized variants show increased enzymatic activity relative to the parent after incubation on the detection media.

To screen for variants with altered thermostability, filters with bound variants are incubated in buffer at a given pH (e.g., in the range from pH 2–12) at an elevated temperature (e.g., in the range from 50°–110° C.) for a time period (e.g., from 1–20 minutes) to inactivate nearly all of the parent CGTase, rinsed in water, then placed directly on a detection plate containing immobilized Cibacron Red labeled amylopectin and incubated until activity is detectable. Similarly, pH dependent stability can be screened for by adjusting the pH of the buffer in the above inactivation step such that the parent CGTase is inactivated, thereby allowing detection of only those variants with increased stability at the pH in question. To screen for variants with increased calcium-dependent stability calcium chelators, such as ethylene glycol-bis(β-aminoethyl ether) N,N,N',N'-tetraacetic acid (EGTA), is added to the inactivation buffer at a concentration such that the parent CGTase is inactivated under conditions further defined, such as buffer pH, temperature or a specified length of incubation.

The variants of the invention may be suitably tested by assaying the starch-degrading activity of the variant, for instance by growing host cells transformed with a DNA sequence encoding a variant on a starch-containing agarose plate and identifying starch-degrading host cells as described above. Further testing in regard to altered properties, including specific activity, substrate specificity, cleavage pattern, thermoactivation, thermostability, pH dependent activity or optimum, pH dependent stability, temperature dependent activity or optimum, transglycosylation activity, stability, and any other parameter of interest, may be performed on purified variants in accordance with methods known in the art as described below.

The maltogenic alpha-amylase activity of variants of the invention towards linear maltodextrins and cyclodextrins may be assayed by measuring the hydrolysis of maltotriose. Hydrolysis is monitored by the formation of glucose using the GLU-kit (Boehringer Mannheim, Indianapolis Ind.). Hydrolysis of longer maltodextrins, such as malto-tetraose to -heptaose) and cyclodextrins is monitored by the formation of free reducing ends which is measured spectrophotometrically.

Alternatively, amylolytic activity can be assayed using the Phadebas method (BioRad, Inc., Richmond, Calif.) in which the substrate is a water-insoluble cross-linked starch polymer carrying a blue dye (Phadebas Amylase Test) that is hydrolyzed by amylolytic activity to form water-soluble blue fragments which can then be quantitated spectrophotometrically.

In cases where the variants of the invention have been altered in the substrate binding site, it may be desirable to determine whether such variant is capable of performing a transglycosylation reaction, which is described below in Example 1, as is normally observed for CGTases.

Substrate specificity of maltogenic alpha-amylase variants may be assayed by measuring the degree to which such enzymes are capable of degrading starch that has been exhaustively treated with the exoglycosylase β-amylase. To screen for variants which show patterns of degradation on such a substrate differing from the patterns produced by the parent CGTase the following assay is performed: β-limit dextrin is prepared by incubating 25 ml 1% amylopectin in McIlvane buffer (48.5 mM citrate and 193 mM sodium phosphate pH 5.0) with 24 pg/ml -amylase overnight at 30° C. Unhydrolysed amylopectin (i.e., β-limit dextrin) is precipitated with 1 volume 98% ethanol, washed and redissolved in water. 1 ml β-limit dextrin is incubated with 18 μl enzymes (at 2.2 mg/ml) and 100 μl 0.2 M citrate-phosphate pH 5.0 for 2 hrs at 30° C. and analysed by HPLC as described above. Total hydrolysis of β-limit dextrin is carried out in 2M HCl at 95° C. The concentration of reducing ends is measured by methods known in the art.

INDUSTRIAL APPLICATIONS

The maltogenic alpha-amylase variants of the invention possess valuable properties which may be advantageously used in various industrial applications. In particular, the enzyme finds potential application for retarding or preventing retrogradation, and thus the staling, of starch based food common in the baking industry.

The variant may be used for the preparation of bread and other bread products in accordance with conventional techniques known in the art.

It is believed that the modification of the starch fraction by use of the present invention results in increased volume in baked products and improved organoleptic qualities, such as flavor, mouth feel, palatability, aroma and crust color.

The maltogenic alpha-amylase variant may be used as the only enzyme or as a major enzymatic activity in combination with one or more additional enzymes, such as xylanase, lipase, glucose oxidase and other oxidoreductases, or an amylolytic enzyme.

The enzyme variants of the invention also find industrial applicability as a component in washing, dishwashing and hard-surface cleaning detergent compositions. Some variants are particularly useful in a process for the manufacture of linear oligosaccharides, or in the production of sweeteners and ethanol from starch, and/or for textile desizing. Conditions for conventional starch conversion processes, including starch liquefaction and/or saccharification processes, are described in, e.g., U.S. Pat. No. 3,912,590 and in EP patent publications Nos. 252,730 and 63,909.

The variants of the invention also find application in processes for the manufacture of cyclodextrins for various industrial applications, particularly in the food, cosmetic, chemical, agrochemical and pharmaceutical industries.

Therefore in another aspect the invention provides maltogenic alpha-amylase variants for use in a process for the manufacture of cyclodextrins, in particular α-, β-, γ-, δ-, ε-, and/or ζ-cyclodextrins. In a more preferred embodiment, the invention provides maltogenic alpha-amylase variants for use in a process for the manufacture of α-, β- and γ-cyclodextrins, or mixtures hereof.

In yet another preferred embodiment, the variants of the invention may be used for in situ generation of cyclodextrins. In this way the variants of the invention may be added to a substrate containing medium in which the enzyme variants are capable of forming the desired cyclodextrins. This application is particularly well suited for use in methods of producing baked products as described above, in methods for stabilizing chemical products during their manufacture, and in detergent compositions.

Cyclodextrins have an inclusion ability useful for stabilization, solubilization, etc. Thus cyclodextrins can make oxidizing and photolytic substances stable, volatile substances non-volatile, poorly-soluble substances soluble, and odoriferous substances odorless, etc. and thus are useful to encapsulate perfumes, vitamins, dyes, pharmaceuticals, pesticides and fungicides. Cyclodextrins are also capable of binding lipophilic substances such as cholesterol, to remove them from egg yolk, butter, etc.

Cyclodextrins also find utilization in products and processes relating to plastics and rubber, where they have been used for different purposes in plastic laminates, films, membranes, etc. Also, cyclodextrins have been used for the manufacture of biodegradable plastics.

EXAMPLES

The invention is further illustrated with reference to the following examples which are not intended to be in any way limiting to the scope of the invention as claimed.

Example 1

Construction of Variants of Thermoanaerobacter CGTase with Altered Substrate Specificity This example describes the construction of CGTase variants with modified substrate specificity. The variants are derived from a parent Thermoanaerobacter sp. CGTase (i.e. the wild type), obtained as described in WO 89/03421 and WO 96/33267.

Bacterial Strains, Plasmids and Growth Conditions

Escherichia coli ME32 was used for recombinant DNA manipulations. The variants were expressed in SHA273, a derivative of Bacillus subtilis 168 which is apr, npr$^-$, amyE$^-$, amyR2$^-$ and prepared by methods known in the art. pCA31-wt is a E coli-B. subtilus shuttle vector harboring the parent Thermoanaerobacter CGTase, shown in FIG. 1.

DNA Manipulations

DNA manipulations and transformation of E. coli were essentially as described in Sambrook, J., Fritsch, E. J., and Maniatis, T. (1989) *Molecular cloning: a laboratory manual*, Cold Spring Harbor Laboratory Press, New York. B. subtilis was transformed using methods known in the art.

Site-directed Mutagenesis

Mutant CGTase genes were constructed via SOE-PCR method (Nelson and Long, op.cit.) using the Pwo DNA polymerase (Boehringer Mannheim, Indianapolis, Ind.). The primary PCR reactions were carried out with the mutagenesis primers 1 and 2 (SEQ ID NO: 3 and 4) plus an upstream or a downstream primer (SEQ ID NO: 5 or 6) on the template strand, respectively. The reaction products were subsequently used as template in a second PCR reaction together with the upstream and downstream primers. The product of the last reaction was digested with StyI and SpeI, and exchanged with the corresponding fragment (640 bp) from the vector pCA31-wt or pCA31-Δ(87–94) (T-CGTase+ L82H+D84*+T84bG+F84cY+G84d*+G85*+S86*). The resulting variant plasmids were transformed into E. coli ME32 and vector DNA was purified from E. coli colonies using the DNA-purification kit from QIAGEN (Qiagen, Inc. Germany). The mutant vectors were finally transformed into B. subtilis SHA273 for enzyme expression.

The degeneration of mutagenesis primer 2 (SEQ ID NO: 4) containing A or C/G gave rise to two different amino acid sequences. Thus, two variants of a parent CGTase were constructed. Successful mutations resulted in restriction sites (Sac II) at positions 7–12 of SEQ ID NO: 3 and positions 2–7 of SEQ ID NO: 4, which allowed quick screening of transformants. Mutations were verified by standard DNA sequencing techniques. The correctness of the StyI-SpeI fragment obtained by PCR was also confirmed by DNA sequencing.

Production and Purification of CGTase Proteins

Enzymes were produced in transformed SHA273 cells grown in shakeflasks at 30–37° C. in 2*TY media containing 10 μg/l kanamycin. After 68–72 h of growth the culture was pelleted and the supernatant separated from the cells by centrifugation. Afer filtration through a 0.45 μm nitrocellulose filter, the supernatant was directly applied to an α-cyclodextrin-sepharose-6FF affinity column (Monma et al. 1988 *Biotechnol. Bioeng.* 32, 404–407). After washing the column with 10 mM sodium acetate (pH 5.5), the variants were eluted with the same buffer supplemented with 1% (w/v) α-cyclodextrin. Purity and molecular weight of the variants obtained were checked by SDS-PAGE. Protein concentrations were determined by measuring the absorption at 280 nm using a theoretical extinction coefficient at 1.74 ml/mg$^{-1}$/cm$^{-1}$.

Enzyme Assays

All assays were performed at pH 6.0 and 37° C. The assay for cyclization activity was performed as described by Penninga et al (1995, *Biochemistry* 34:3368–3376). Starch liquefying activity was measured using the Phadebas Amylase Test kit (Pharmacia A/B, Sweden). Transglycosylation activity was assayed in which 2.2 μM of the variant was incubated with 200 mM maltotriose at 40° C. in 10 mM NaOAc pH 5.0 and 1 mM CaCl$_2$. At different time intervals, aliquots were analyzed by HPLC to measure formation of different maltodextrins. Analytical separations of maltodextrins were performed on a Dionex CarboPac PA1-column connected to a Beckman Gold HPLC-system and a pulsed-amperometric detector. The gradient was 0–600 mM NaOAc over 15 minutes in 0.1 M NaOH. Transglycosylation activity was detected as an increase in the size of the from three to greater than three glucose units covalently linked.

Example 2

Specific PCR Amplification using Novamyl-specific PCR Primers

Comparison of Novamyl with CGTases reveals that it is thus far unique in one structural feature: the insertion of a 5 amino acid "loop" in domain A, residues 190 to 194 in the amino acid sequence shown in SEQ ID NO: 1, that affects the enzyme structure near the active site. It is therefore valuable to have a method of obtaining variants with a similar active site structure, especially with respect to the Novamyl active site loop. Here we describe such a method using PCR primers specific to the Novamyl loop to amplify from natural sources only those clones with this unique structural feature.

Step 1. PCR Amplification of Glycosylases with Degenerate Primers

Alignment of amino acid sequences for Novamyl with known CGTases reveals regions of high homology that can be used to design degenerate oligonucleotide primers for use in the PCR amplification of CGTases from a mixed pool of genomic or cDNA. The resulting fragments of a predicted size range can then be used as template DNA in further PCR amplifications with Novamyl loop-specific primers as described in Step 2.

Alignment of 10 amino acid sequences most related to Novamyl was used to identify two regions of high local homology for the design of degenerate primers: Primer 1 (SEQ ID NO: 7) corresponsing to amino acids 88–93 from SEQ ID NO: 1 and Primer 2 (SEQ ID NO: 8) corresponding to amino acids 417–412 from SEQ ID NO: 1.

Use of these primers on DNA fragments from bacterial sources can, when used as primers in a PCR reaction under standard conditions, amplify a DNA fragment approximately 1,000 basepairs in length containing the central core of related glycosylases. Resulting PCR fragments could then be used as templates in step 2, as described below.

Figure 3:
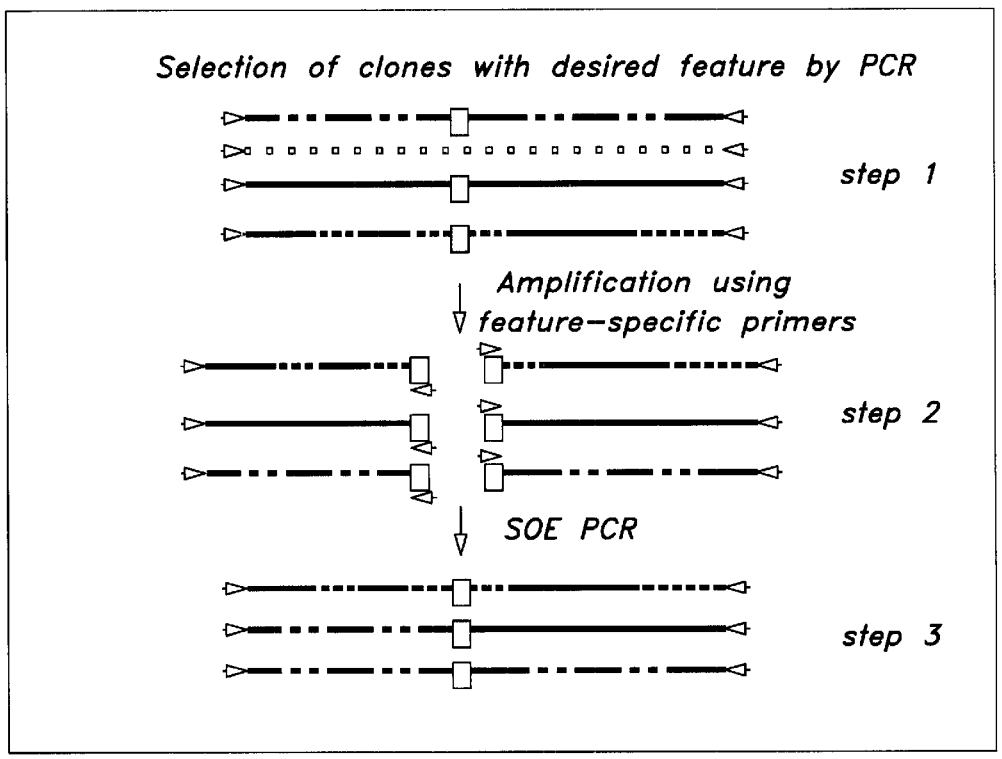
FIG. 3 is a diagram showing the selection of clones with desired features by PCR, as described in Examples 2 and 3.

Step 2. PCR Amplification using Novamyl Loop-specific primers (FIG. 3)

The following primer pair can be used, corresponding to the degenerate translation of the amino acid sequence in the coding (d3, SEQ ID 9) or noncoding (d4, SEQ ID NO: 10) DNA strand:

Primer d3 (SEQ ID NO: 9): degenerate sense primer corresponding to amino acids 190–194 from SEQ ID NO: 1.

Primer d4 (SEQ ID NO: 10): degenerate anti-sense primer corresponding to amino acids 194–190 from SEQ ID NO: 1.

Alternatively, it is possible to use the degenerate or exact nucleotide sequence of Novamyl through eight amino acids that contain the Novamyl sequence, Phe188-Thr189-Asp190-Pro191-Ala192-Gly193-Phe194-Ser195 (loop underlined) in both DNA strands as primers in a PCR reaction:

Primer d5 (SEQ ID NO: 11): degenerate sense primer corresponding to amino acids 188–193 from SEQ ID NO: 1.

Primer d6 (SEQ ID NO: 12): degenerate anti-sense primer corresponding to amino acids 195–190 from SEQ ID NO: 1.

Primer 7 (SEQ ID NO: 13): Exact Novamyl sense primer corresponding to amino acids 188–193 from SEQ ID NO: 1.

Primer 8 (SEQ ID NO: 14): Exact Novamyl anti-sense primer corresponding to amino acids 195–190 from SEQ ID NO: 1.

Using the PCR products of step 1 as templates in a PCR reaction together with primer pairs 1 and d4, 2 and d4, 1 and d5, 2 and d6, 1 and 7, or 2 and 8, only those DNA sequences encoding the Novamyl loop are expected to produce DNA fragments of approximately the predicted size (FIG. 1, step 2.). Templates lacking the loop-encoding DNA will not produce a product under standard PCR conditions with an annealing temperature of 58° C.

| Product | Primer pair | approximate size of product |
|---|---|---|
| A1 | 1 + d4 | 321 |
| A2 | 1 + d6 | 324 |
| A3 | 1 + 8 | 324 |
| B1 | 2 + d3 | 684 |
| B2 | 2 + d5 | 690 |
| B3 | 2 + 7 | 690 |

Step 3. Reconstruction of Full-length Fragments

Step 2 yields partial coding sequences of glycosylases that contain the Novamyl loop at either the 3' (A fragments) or 5' ends (B fragments) of the DNA fragments. Reassembly of longer clones containing the loop will require the combining of the A and B fragments by SOE-PCR methods known in the art.

Example 3

Conversion of CGTases into Novamyl-like Enzymes by Random Re-combination

In this example, the unique active site loop was used to select hybrid enzymes with maltogenic alpha-amylase activity from a library of random recombinants. In this method, Novamyl and the cyclic maltodextrin glucosyl transferase (CGTase) from *Bacillus circulans,* were randomly recombined by the DNA shuffling method of Crameri A, et al., op.cit. Those resulting mutants containing the Novamyl loop were selected using PCR as described above in Example 2.

Figure 2:
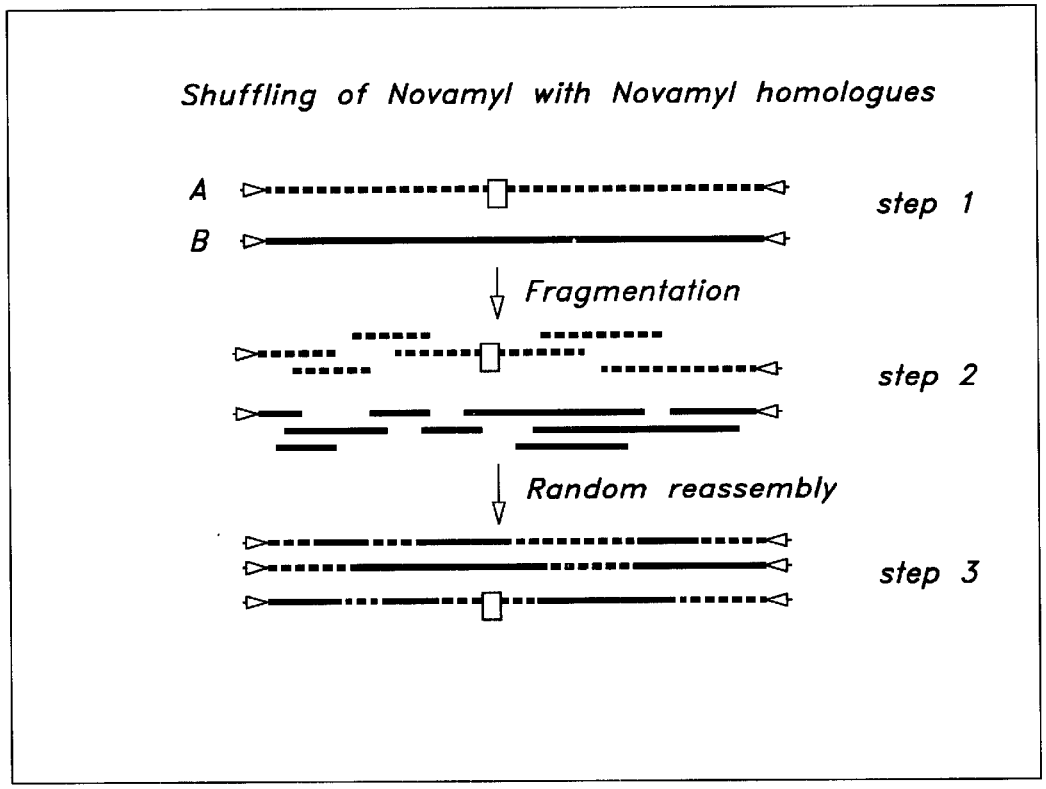
FIG. 2 is a diagram showing the shuffling of Novamyl with CGTases, as described in Example 3.

Step 1. PCR amplification and Shuffling of Novamyl and CGTase (FIG. 2)

Specific oligonucleotide primers specific for either the Novamyl coding sequence or the CGTase coding sequenced were designed as shown in SEQ ID NO: 15–20.

The entire Novamyl coding sequence (lacking the signal sequence) was amplified using the Novamyl-specific primer pair #9 and #10 (SEQ ID NO: 15 and 16). Similarly, the mature CGTase coding sequence was amplified using the CGTase-specific primer pair #11 and #12 (SEQ ID NO: 17 and 18). Both amplifications were performed using the following reaction conditions: 100 µM each primer, 0.2 mM each of dATP, dCTP, dGTP, and TTP, 2.5 U AmpliTaq polymerase (Perkin Elmer, Inc.), and 1× concentration of the buffer supplied by the manufacturer. PCR was performed in a Perkin Elmer Thermocycler, model 2400, with the following conditions: 5 minutes at 94 C. 25 cycles of 30 seconds at 94 C., 1 minute at 58 C., and 2 minutes at 72 C. followed by a final incubation of 7 minutes at 72° C.

The resulting PCR products were then subjected to DNA shuffling as described by Stemmer et al. Briefly, the two DNA fragments were mixed in equimolar amounts and randomly digested using DNase I treatment to generate gene fragments of between 50 and 500 bp. These gene fragments were then allowed to anneal to one another and extend in a PCR reaction under low stringency conditions, resulting in a re-assembling of an intact gene pool containing the reassemble parental DNAs as well as chimeras between the parents. Final amplification of shuffled products was performed using the general primer pair #13 and #14 (SEQ ID NO: 19 and 20) using the PCR conditions described above. Using these primers, all full-length species, both parental and chimeric, were amplified.

Step 2. PCR Amplification using Novamyl Loop-specific Primers (FIG. 3)

Those genes within this mixture containing the Novamyl loop were then selected for as described in Example 2 using the loop-specific primers. In the first round of amplification, the 5' and 3' ends of the genes containing the loop were amplified by using the general primers in combination with the loop specific primers #7 and #8 (SEQ ID NO: 13 and 14) to amplify either the 5' ends of the genes extending to the loop-encoding sequence #13 and #8 (SEQ ID NO: 19 and 14) or the sequence extending from the loop to the 3' ends of the genes #7 and #14 (SEQ ID NO: 13 and 20). As described in Example 2, the resulting fragments were then assembled using SOE PCR to create full-length genes. These products were then selectively amplified using primer pairs lacking a Novamyl-specific primer to produce only chimeras: #11, #10 and #12 (SEQ ID NO: 17, 16 and 18) or #10, #9 and #11 (SEQ ID NO: 16, 15 and 17). In this way, only those clones that contained either the CGTase 5' end and the Novamyl loop or the CGTase 3' end and the Novamyl loop were selected.

The final PCR product were then digested with the enzymes Xba I and Mlu I and inserted into a vector containing an intact signal sequence. The resulting clones were transformed into Bacillus, and the resulting polypeptides were sequenced.

3 polypeptides obtained by this method were found to be hybrids containing an N-terminal sequence from Novamyl and a C-terminal sequence from the *B. circulans* CGTase as follows:

Novamyl amino acids 1–196+CGTase amino acids 198–685

Novamyl amino acids 1–230+CGTase amino acids 232–685

Novamyl amino acids 1–590+CGTase amino acids 596–685.

These results demonstrate that the method is effective for generating and selecting hybrids.

Example 4

Construction of a Variant of Novamyl with CGTase Activity

A variant of Novamyl was constructed that has an altered substrate specificity relative to the parent enzyme, in which the variant has a CGTase-like transglycosylation/cyclization activity not detectable in the parent enzyme. The variant differs from the parent Novamyl with the amino acid sequence shown in amino acids 1–686 of SEQ ID NO: 1 in that residues 191–195 were removed, Phe188 was substituted with Leu and Thr189 was substituted with Tyr, termed Δ (191–195)-F188L-T189Y. The variant was constructed by sequence overlap extension PCR (SOE PCR) essentially as described by Nelson and Long (op.cit.). SOE PCR consists of two primary PCRs that produce two overlapping PCR fragments, both bearing the same modification(s). In a second round of PCR, the two products from the two primary PCRs are mixed without addition of template DNA.

Oligonucleotide primers used in the construction of Δ (191–195)-F188L-T189Y:

Mutagenic Primer 1 (SEQ ID NO: 21) and Primer 2 (SEQ ID NO: 22). Positions 16–21 of SEQ ID NO: 21 and positions 4–9 of SEQ ID NO: 22 are restriction sites.

The Δ (191–195)-F188L-T189Y were obtained using oligomers A82 (SEQ ID NO: 23) and B346 (SEQ ID NO: 24) as end-primers.

DNA manipulations, transformation of *Bacillus subtilis*, and purification of the resulting variant was performed as described above in Example 4. The final purified variant was analysed for the ability to form cyclodextrin from linear starch and compared to the parent Novamyl enzyme as described below.

Detection of β-cyclodextrin

The variant and the parent Novamyl enzyme were diluted with 10 mM citrate buffer pH 6.0 in order to obtain an equivalent protein concentration prior to assay.

The cyclisation reaction mixture in a final volume of 1 ml contained:

0–50 µl enzyme or variant diluted in 10 mM sodium citrate buffer pH 6.0

500 µl 10%(w/v) Paselli SA2 (AVEBE, Foxhol, The Netherlands) dissolved in 10 mM citrate buffer pH 6.0 for a final solution of 5%.

The reaction mixture was pre-incubated in a 50° C. water bath for 10 min. before adding the enzyme or variant, and at one-min time intervals a 100 µl sample was put on ice for further analysis.

β-cyclodextrin was quantitated on the basis of formation of a stable colourless inclusion complex with phenolphthalein; thus, the colour of the solution decreases with as the amount of β-cyclodextrin detected increases.

To each of the 100 µl samples from the cyclization reaction 900 µl of a working solution (3 ml of 3.75 mM phenolphthalein added to 100ml 0.2 M $Na_2CO_3$, pH 9.7) was added, and the absorbance immediately read at 552 nm. β-cyclodextrin was quantitated on the basis of a calibration curve prepared in a final volume of one-ml as follows:

0–50 µl 2 mM β-cyclodextrin (0–100 nmol)

50–0 µl milli-Q water

900 µl working solution

50 µl 10% Pasellie SA2

A new calibration curve was made for each new preparation of Paselli SA2 solution.

The results of the cyclization assay are presented in the table below as β-cyclodextrin formation (mmol/mg enzyme) for the variant Δ (191–195)-F188L-T189Y and for the parent enzyme, Novamyl:

| Time (min) | Variant | Novamyl |
| --- | --- | --- |
| 0 | 0 | 0 |
| 2 | 160 | 0 |
| 3 | 230 | 0 |
| 4 | 240 | 0 |
| 5 | 320 | 0 |
| 6 | 380 | 0 |
| 7 | 390 | 0 |
| 8 | 500 | 0 |
| 10 | 680 | 0 |

The results clearly demonstrate that the variant, unlike the parent Novamyl enzyme, can form β-cyclodextrin.

Example 5

Construction of a CGTase Variant with Ability to Form Linear Oligosaccharides

This example describes the construction of a CGTase variant derived from a parent Thermoanaerobacter CGTase.

Mutant CGTase genes were constructed via SOE-PCR method as described in Example 1. The primary PCR reactions were carried out with the mutagenesis primers A91 (SEQ ID NO: 26) and A90 (SEQ ID NO: 25) plus an upstream or a downstream primer (SEQ ID NO 5 or 6) on the template strand, respectively. The product of the last reaction was digested with BST1107 I and Pst I, and exchanged with the corresponding fragment (250 bp) from the vector pCA31-wt or pCA31-(T-CGTase+F189L+*190D+*191P+*192A+*193G+*194F+D195S). Successful mutations resulted in restriction sites (Xma I) at positions 4–9 of A91 (SEQ ID NO: 26) and positions 11–16 of A90 (SEQ ID NO: 25), which allowed quick screening of transformants. The following mutations were verified by standard DNA sequencing techniques:

Y260F+L261G+G262D+T263D+N264P+E265G+V266T+*266aA+*266bN+D267H+P268V

*194aT+*194bD+*194cP+*194dA+*194eG+D196S+Y260F+L261G+G262D+T263D+N264P+E265G+V266T+*266aA+*266bN+D267H+P268V

Example 6

Properties of CGTase Variant with Ability to Form Linear Oligosaccharides

Inhibition of Starch Retrogradation

The first variant prepared in Example 5 was tested for its ability to inhibit starch retrogradation was tested as follows:

730 mg of 50% (w/w) amylopectin slurry in 0.1 M sodium acetate, at a selected pH (3.7, 4.3 or 5.5) was mixed with 20 μl of an enzyme sample, and the mixture was incubated in a sealed ampoule for 1 hour at 40° C., followed by incubation at 100° C. for 1 hour in order to gelatinize the samples. The sample was then aged for 7 days at room temperature to allow recrystallization of the amylopectin. A control without enzyme was included.

After aging, DSC was performed on the sample by scanning from 5° C. to 95° C. at a constant scan rate of 90° C./hour. The area under the first endothermic peak in the thermogram was taken to represent the amount of retrograded amylopectin, and the relative inhibition of retrogradation was taken as the area reduction (in %) relative to the control without enzyme.

The result was a relative inhibition of 21%.

Reaction Pattern with Starch

The variant was compared with Novamyl and with Thermoanaerobacter CGTase by determining the reaction products formed after 24 hours incubation in 5% (w/v) amylopectin using 50 mM sodium acetate, 1 mM CaCl2, pH 5.0 at 50° C. The reaction products (in % by weight) were identified and quantitated using HPLC.

| Oligosaccharide | Novamyl | CGTase | Variant |
| --- | --- | --- | --- |
| G10 | — | — | 0.7 |
| G9 | — | — | 1.5 |
| G8 | — | — | 2.4 |
| G7 | — | — | 1.9 |
| G6/α-CD | — | 53.9 | 23.1 |
| G5 | — | — | 6.1 |
| G4 | — | — | 8.1 |
| G3/γ-CD | — | 12.0 | 14.5 |
| G2 | 97.9 | — | 11.5 |
| G1 | 2.1 | — | 6.8 |
| β-CD | — | 34.1 | 23.1 |

The results show clearly that whereas the parent CGTase exclusively forms cyclodextrins, the reaction pattern of the variant has been changed to form both cyclodextrins and linear maltodextrins as initial products.

What is claimed is:

1. A polypeptide which:
   a) has at least 70% identity to amino acids 1–686 of SEQ ID NO: 2;
   b) comprises an amino acid modification which is an insertion, substitution or deletion compared to SEQ ID NO: 2 in a region corresponding to amino acids 40–43, 78–85, 136–139, 173–180, 189–195 or 259–268; and
   c) has the ability to form cyclodextrin when acting on starch.

2. The polypeptide of claim 1 wherein the modification comprises a substitution with or insertion of the amino acid residue present at the corresponding position of a cyclodextrin glucanotransferase (CGTase) or deletion of an amino acid residue which is not present at that position in a cyclodextrin glucanotransferase (CGTase).

3. The polypeptide of claim 2 wherein the CGTase is derived from a strain of Bacillus, Brevibacterium, Clostridium, Corynebacterium, Klebsiella, Micrococcus, Thermoanaerobacter or Thermoanaerobacterium.

4. The polypeptide of claim 1, wherein the modification comprises a deletion in the region 190–195.

5. The polypeptide of claim 1, which further comprises a substitution of amino acid 188 or 189.

6. A polypeptide which:
   a. has an amino acid sequence having at least 70% identity to a parent Bacillus or Thermoanaerobacter cyclodextrin glucanotransferase (CGTase);
   b. comprises an amino acid modification compared to the parent CGTase in a region corresponding to amino acids 40–43, 78–85, 136–139, 173–180, 189–195 or 259–268 of the amino acid sequence shown in SEQ ID NO: 2, wherein the modification comprises a substitution or insertion of an amino acid residue in the region with an amino acid residue of a corresponding position in the amino acid sequence shown in SEQ ID NO: 2 or a deletion of an amino acid residue in the region which is not present at the corresponding position in the amino acid sequence shown in SEQ ID NO: 2, and
   c. has the ability to form linear oligosaccharides as an initial product when acting on starch.

7. The polypeptide of claim 6, wherein the modification is an insertion of the amino acid sequence DPAGF (Asp-Pro-Ala-Gly-Phe) (SEQ ID NO:27) at a position corresponding to D190-F194 of SEQ ID NO: 2.

8. The polypeptide of claim 6, wherein the CGTase is derived from a strain of Bacillus, Brevibacterium, Clostridium, Corynebacterium, Klebsiella, Micrococcus, Thermoanaerobacter or Thermoanaerobacterium.

9. The polypeptide of claim 6, which further comprises a modification in a region corresponding to amino acids 37–39, 44–45, 135, 140–145, 181–186, 269–273, or 377–383 of SEQ ID NO: 2.

10. The polypeptide of claim 1, wherein the modification comprises the deletion (191–195).

11. The polypeptide of claim 1, which further comprises a substitution of F188L or T189Y.

12. The polypeptide of claim 6, wherein the amino acid modification is in a region corresponding to amino acids 40–43 of SEQ ID NO: 2.

13. The polypeptide of claim 6, wherein the amino acid modification is in a region corresponding to amino acids 78–85 of SEQ ID NO: 2.

14. The polypeptide of claim 6, wherein the amino acid modification is in a region corresponding to amino acids 136–139 of SEQ ID NO: 2.

15. The polypeptide of claim 6, wherein the amino acid modification is in a region corresponding to amino acids 173–180 of SEQ ID NO: 2.

16. The polypeptide of claim 6, wherein the amino acid modification is in a region corresponding to amino acids 189–195 of SEQ ID NO: 2.

17. The polypeptide of claim 6, wherein the amino acid modification is in a region corresponding to amino acids or 259–268 of SEQ ID NO: 12.

18. The polypeptide of claim 6, wherein the amino acid modification comprises an insertion of 3–7 amino acids in a region corresponding to amino acids 190–194 of SEQ ID NO:2.

19. The polypeptide or claim 18, wherein the amino acid modification further comprises a substitution at the position corresponding to position T189 of SEQ ID NO:2.

20. A polypeptide which:
   a. has an amino acid sequence having at least 70% identity to a parent Bacillus or Thermoanerobacter cyclodextrin glucanotransferase (CGTase);
   b. comprises an amino acid modification compared to the parent CGTase of an insertion of 3–7 amino acids in a region corresponding to amino acids 190–194 of the amino acid sequence shown in SEQ ID NO:2, and
   c. has the ability to form linear oligosaccharides as an initial product when acting on starch.

21. The polypeptide of claim 20, wherein the amino acid modification comprises an insertion of 4–6 amino acids in a region corresponding to amino acids 190–194 of SEQ ID NO:2.

22. The polypeptide of claim 20, wherein the amino acid modification comprises an insertion of 5 amino acids in a region corresponding to amino acids 190–194 of SEQ ID NO:2.

23. The polypeptide of claim 20, wherein the amino acid modification comprises an insertion of DPAGF in a region corresponding to amino acids 190–194 of SEQ ID NO:2.

24. The polypeptide of claim 20, wherein the amino acid modification further comprises a substitution at a position corresponding to T189 of SEQ ID NO:2.

* * * * *

SEQUENCE LISTING

```
<160> NUMBER OF SEQ ID NOS: 31

<210> SEQ ID NO 1
<211> LENGTH: 2160
<212> TYPE: DNA
<213> ORGANISM: Bacillus sp.
<220> FEATURE:
<221> NAME/KEY: CDS
<222> LOCATION: (1)..(2157)
<223> OTHER INFORMATION:
<220> FEATURE:
<221> NAME/KEY: mat_peptide
<222> LOCATION: (100)..()
<223> OTHER INFORMATION:

<400> SEQUENCE: 1 atg aaa aag aaa acg ctt tct tta ttt gtg gga ctg atg ctc ctc atc      48
Met Lys Lys Lys Thr Leu Ser Leu Phe Val Gly Leu Met Leu Leu Ile
            -30                 -25                 -20
```

-continued

| | | |
|---|---|---|
| ggt ctt ctg ttc agc ggt tct ctt ccg tac aat cca aac gcc gct gaa<br>Gly Leu Leu Phe Ser Gly Ser Leu Pro Tyr Asn Pro Asn Ala Ala Glu<br>      -15                   -10                  -5 | | 96 |
| gcc agc agt tcc gca agc gtc aaa ggg gac gtg att tac cag att atc<br>Ala Ser Ser Ser Ala Ser Val Lys Gly Asp Val Ile Tyr Gln Ile Ile<br>-1  1                  5                    10                  15 | | 144 |
| att gac cgg ttt tac gat ggg gac acg acg aac aac aat cct gcc aaa<br>Ile Asp Arg Phe Tyr Asp Gly Asp Thr Thr Asn Asn Asn Pro Ala Lys<br>              20                    25                  30 | | 192 |
| agt tat gga ctt tac gat ccg acc aaa tcg aag tgg aaa atg tat tgg<br>Ser Tyr Gly Leu Tyr Asp Pro Thr Lys Ser Lys Trp Lys Met Tyr Trp<br>              35                    40                  45 | | 240 |
| ggc ggg gat ctg gag ggg gtt cgt caa aaa ctt cct tat ctt aaa cag<br>Gly Gly Asp Leu Glu Gly Val Arg Gln Lys Leu Pro Tyr Leu Lys Gln<br>        50                    55                  60 | | 288 |
| ctg ggc gta acg aca atc tgg ttg tcc ccg gtt ttg gac aat ctg gat<br>Leu Gly Val Thr Thr Ile Trp Leu Ser Pro Val Leu Asp Asn Leu Asp<br>    65                    70                  75 | | 336 |
| aca ctg gcg ggc acc gat aac acg ggc tat cac gga tac tgg acg cgc<br>Thr Leu Ala Gly Thr Asp Asn Thr Gly Tyr His Gly Tyr Trp Thr Arg<br>80                  85                  90                  95 | | 384 |
| gat ttt aaa cag att gag gaa cat ttc ggg aat tgg acc aca ttt gac<br>Asp Phe Lys Gln Ile Glu Glu His Phe Gly Asn Trp Thr Thr Phe Asp<br>              100                   105               110 | | 432 |
| acg ttg gtc aat gat gct cac caa aac gga atc aag gtg att gtc gac<br>Thr Leu Val Asn Asp Ala His Gln Asn Gly Ile Lys Val Ile Val Asp<br>            115                   120               125 | | 480 |
| ttt gtg ccc aat cat tcg act cct ttt aag gca aac gat tcc acc ttt<br>Phe Val Pro Asn His Ser Thr Pro Phe Lys Ala Asn Asp Ser Thr Phe<br>        130                   135               140 | | 528 |
| gcg gaa ggc ggc gcc ctc tac aac aat gga acc tat atg ggc aat tat<br>Ala Glu Gly Gly Ala Leu Tyr Asn Asn Gly Thr Tyr Met Gly Asn Tyr<br>        145                   150               155 | | 576 |
| ttt gat gac gca aca aaa ggg tac ttc cac cat aat ggg gac atc agc<br>Phe Asp Asp Ala Thr Lys Gly Tyr Phe His His Asn Gly Asp Ile Ser<br>160                  165                  170               175 | | 624 |
| aac tgg gac gac cgg tac gag gcg caa tgg aaa aac ttc acg gat cca<br>Asn Trp Asp Asp Arg Tyr Glu Ala Gln Trp Lys Asn Phe Thr Asp Pro<br>              180                   185               190 | | 672 |
| gcc ggt ttc tcg ctt gcc gat ttg tcg cag gaa aat ggc acg att gct<br>Ala Gly Phe Ser Leu Ala Asp Leu Ser Gln Glu Asn Gly Thr Ile Ala<br>            195                   200               205 | | 720 |
| caa tac ctg acc gat gcg gcg gtt caa ttg gta gca cat gga gcg gat<br>Gln Tyr Leu Thr Asp Ala Ala Val Gln Leu Val Ala His Gly Ala Asp<br>        210                   215               220 | | 768 |
| ggt ttg cgg att gat gcg gtg aag cat ttt aat tcg ggg ttc tcc aaa<br>Gly Leu Arg Ile Asp Ala Val Lys His Phe Asn Ser Gly Phe Ser Lys<br>        225                   230               235 | | 816 |
| tcg ttg gcc gat aaa ctg tac caa aag aaa gac att ttc ctg gtg ggg<br>Ser Leu Ala Asp Lys Leu Tyr Gln Lys Lys Asp Ile Phe Leu Val Gly<br>240                  245                  250               255 | | 864 |
| gaa tgg tac gga gat gac ccc gga aca gcc aat cat ctg gaa aag gtc<br>Glu Trp Tyr Gly Asp Asp Pro Gly Thr Ala Asn His Leu Glu Lys Val<br>              260                   265               270 | | 912 |
| cgg tac gcc aac aac agc ggt gtc aat gtg ctg gat ttt gat ctc aac<br>Arg Tyr Ala Asn Asn Ser Gly Val Asn Val Leu Asp Phe Asp Leu Asn<br>        275                   280               285 | | 960 |
| acg gtg att cga aat gtg ttc ggc aca ttt acg caa acg atg tac gat<br>Thr Val Ile Arg Asn Val Phe Gly Thr Phe Thr Gln Thr Met Tyr Asp<br>            290                   295               300 | | 1008 |

```
ctt aac aat atg gtg aac caa acg ggg aac gag tac aaa tac aaa gaa    1056
Leu Asn Asn Met Val Asn Gln Thr Gly Asn Glu Tyr Lys Tyr Lys Glu
    305                 310                 315 aat cta atc aca ttt atc gat aac cat gat atg tca aga ttt ctt tcg    1104
Asn Leu Ile Thr Phe Ile Asp Asn His Asp Met Ser Arg Phe Leu Ser
320                 325                 330                 335 gta aat tcg aac aag gcg aat ttg cac cag gcg ctt gct ttc att ctc    1152
Val Asn Ser Asn Lys Ala Asn Leu His Gln Ala Leu Ala Phe Ile Leu
                340                 345                 350 act tcg cgg ggt acg ccc tcc atc tat tat gga acc gaa caa tac atg    1200
Thr Ser Arg Gly Thr Pro Ser Ile Tyr Tyr Gly Thr Glu Gln Tyr Met
            355                 360                 365 gca ggc ggc aat gac ccg tac aac cgg ggg atg atg ccg gcg ttt gat    1248
Ala Gly Gly Asn Asp Pro Tyr Asn Arg Gly Met Met Pro Ala Phe Asp
        370                 375                 380 acg aca acc acc gcc ttt aaa gag gtg tca act ctg gcg ggg ttg cgc    1296
Thr Thr Thr Thr Ala Phe Lys Glu Val Ser Thr Leu Ala Gly Leu Arg
    385                 390                 395 agg aac aat gcg gcg atc cag tac ggc acc acc acc cag cgt tgg atc    1344
Arg Asn Asn Ala Ala Ile Gln Tyr Gly Thr Thr Thr Gln Arg Trp Ile
400                 405                 410                 415 aac aat gat gtt tac att tat gaa cgg aaa ttt ttc aac gat gtc gtg    1392
Asn Asn Asp Val Tyr Ile Tyr Glu Arg Lys Phe Phe Asn Asp Val Val
                420                 425                 430 ttg gtg gcc atc aat cga aac acg caa tcc tcc tat tcg att tcc ggt    1440
Leu Val Ala Ile Asn Arg Asn Thr Gln Ser Ser Tyr Ser Ile Ser Gly
            435                 440                 445 ttg cag acg gcc ttg cca aat ggc agc tat gcg gat tat ctg tca ggg    1488
Leu Gln Thr Ala Leu Pro Asn Gly Ser Tyr Ala Asp Tyr Leu Ser Gly
        450                 455                 460 ctg ttg ggg ggg aac ggg att tcc gtt tcc aat gga agt gtc gct tcg    1536
Leu Leu Gly Gly Asn Gly Ile Ser Val Ser Asn Gly Ser Val Ala Ser
    465                 470                 475 ttc acg ctt gcg cct gga gcc gtg tct gtt tgg cag tac agc aca tcc    1584
Phe Thr Leu Ala Pro Gly Ala Val Ser Val Trp Gln Tyr Ser Thr Ser
480                 485                 490                 495 gct tca gcg ccg caa atc gga tcg gtt gct cca aat atg ggg att ccg    1632
Ala Ser Ala Pro Gln Ile Gly Ser Val Ala Pro Asn Met Gly Ile Pro
                500                 505                 510 ggt aat gtg gtc acg atc gac ggg aaa ggt ttt ggg acg acg cag gga    1680
Gly Asn Val Val Thr Ile Asp Gly Lys Gly Phe Gly Thr Thr Gln Gly
            515                 520                 525 acc gtg aca ttt ggc gga gtg aca gcg act gtg aaa tcc tgg aca tcc    1728
Thr Val Thr Phe Gly Gly Val Thr Ala Thr Val Lys Ser Trp Thr Ser
        530                 535                 540 aat cgg att gaa gtg tac gtt ccc aac atg gcc gcc ggg ctg acc gat    1776
Asn Arg Ile Glu Val Tyr Val Pro Asn Met Ala Ala Gly Leu Thr Asp
    545                 550                 555 gtg aaa gtc acc gcg ggt gga gtt tcc agc aat ctg tat tct tac aat    1824
Val Lys Val Thr Ala Gly Gly Val Ser Ser Asn Leu Tyr Ser Tyr Asn
560                 565                 570                 575 att ttg agt gga acg cag aca tcg gtt gtg ttt act gtg aaa agt gcg    1872
Ile Leu Ser Gly Thr Gln Thr Ser Val Val Phe Thr Val Lys Ser Ala
                580                 585                 590 cct ccg acc aac ctg ggg gat aag att tac ctg acg ggc aac ata ccg    1920
Pro Pro Thr Asn Leu Gly Asp Lys Ile Tyr Leu Thr Gly Asn Ile Pro
            595                 600                 605 gaa ttg ggg aat tgg agc acg gat acg agc gga gcc gtt aac aat gcg    1968
Glu Leu Gly Asn Trp Ser Thr Asp Thr Ser Gly Ala Val Asn Asn Ala
```

```
                610                615                620
caa ggg ccc ctg ctc gcg ccc aat tat ccg gat tgg ttt tat gta ttc    2016
Gln Gly Pro Leu Leu Ala Pro Asn Tyr Pro Asp Trp Phe Tyr Val Phe
        625                630                635 agc gtt cca gca gga aag acg att caa ttc aag ttc ttc atc aag cgt    2064
Ser Val Pro Ala Gly Lys Thr Ile Gln Phe Lys Phe Phe Ile Lys Arg
640                645                650                655 gcg gat gga acg att caa tgg gag aat ggt tcg aac cac gtg gcc aca    2112
Ala Asp Gly Thr Ile Gln Trp Glu Asn Gly Ser Asn His Val Ala Thr
                660                665                670 act ccc acg ggt gca acc ggt aac att act gtt acg tgg caa aac tag    2160
Thr Pro Thr Gly Ala Thr Gly Asn Ile Thr Val Thr Trp Gln Asn
        675                680                685

<210> SEQ ID NO 2
<211> LENGTH: 719
<212> TYPE: PRT
<213> ORGANISM: Bacillus sp.

<400> SEQUENCE: 2

Met Lys Lys Thr Leu Ser Leu Phe Val Gly Leu Met Leu Leu Ile
        -30                -25                -20

Gly Leu Leu Phe Ser Gly Ser Leu Pro Tyr Asn Pro Asn Ala Ala Glu
        -15                -10                -5

Ala Ser Ser Ser Ala Ser Val Lys Gly Asp Val Ile Tyr Gln Ile Ile
-1  1                5                 10                15

Ile Asp Arg Phe Tyr Asp Gly Asp Thr Thr Asn Asn Asn Pro Ala Lys
                20                25                30

Ser Tyr Gly Leu Tyr Asp Pro Thr Lys Ser Lys Trp Lys Met Tyr Trp
        35                40                45

Gly Gly Asp Leu Glu Gly Val Arg Gln Lys Leu Pro Tyr Leu Lys Gln
        50                55                60

Leu Gly Val Thr Thr Ile Trp Leu Ser Pro Val Leu Asp Asn Leu Asp
65                70                75

Thr Leu Ala Gly Thr Asp Asn Thr Gly Tyr His Gly Tyr Trp Thr Arg
80                85                90                95

Asp Phe Lys Gln Ile Glu Glu His Phe Gly Asn Trp Thr Thr Phe Asp
                100                105                110

Thr Leu Val Asn Asp Ala His Gln Asn Gly Ile Lys Val Ile Val Asp
                115                120                125

Phe Val Pro Asn His Ser Thr Pro Phe Lys Ala Asn Asp Ser Thr Phe
        130                135                140

Ala Glu Gly Gly Ala Leu Tyr Asn Asn Gly Thr Tyr Met Gly Asn Tyr
        145                150                155

Phe Asp Asp Ala Thr Lys Gly Tyr Phe His His Asn Gly Asp Ile Ser
160                165                170                175

Asn Trp Asp Asp Arg Tyr Glu Ala Gln Trp Lys Asn Phe Thr Asp Pro
                180                185                190

Ala Gly Phe Ser Leu Ala Asp Leu Ser Gln Glu Asn Gly Thr Ile Ala
        195                200                205

Gln Tyr Leu Thr Asp Ala Ala Val Gln Leu Val Ala His Gly Ala Asp
        210                215                220

Gly Leu Arg Ile Asp Ala Val Lys His Phe Asn Ser Gly Phe Ser Lys
        225                230                235

Ser Leu Ala Asp Lys Leu Tyr Gln Lys Lys Asp Ile Phe Leu Val Gly
240                245                250                255
```

-continued

```
Glu Trp Tyr Gly Asp Asp Pro Gly Thr Ala Asn His Leu Glu Lys Val
                260                 265                 270

Arg Tyr Ala Asn Asn Ser Gly Val Asn Val Leu Asp Phe Asp Leu Asn
            275                 280                 285

Thr Val Ile Arg Asn Val Phe Gly Thr Phe Thr Gln Thr Met Tyr Asp
            290                 295                 300

Leu Asn Asn Met Val Asn Gln Thr Gly Asn Glu Tyr Lys Tyr Lys Glu
        305                 310                 315

Asn Leu Ile Thr Phe Ile Asp Asn His Asp Met Ser Arg Phe Leu Ser
320                 325                 330                 335

Val Asn Ser Asn Lys Ala Asn Leu His Gln Ala Leu Ala Phe Ile Leu
                340                 345                 350

Thr Ser Arg Gly Thr Pro Ser Ile Tyr Tyr Gly Thr Glu Gln Tyr Met
                355                 360                 365

Ala Gly Gly Asn Asp Pro Tyr Asn Arg Gly Met Met Pro Ala Phe Asp
            370                 375                 380

Thr Thr Thr Thr Ala Phe Lys Glu Val Ser Thr Leu Ala Gly Leu Arg
        385                 390                 395

Arg Asn Asn Ala Ala Ile Gln Tyr Gly Thr Thr Thr Gln Arg Trp Ile
400                 405                 410                 415

Asn Asn Asp Val Tyr Ile Tyr Glu Arg Lys Phe Phe Asn Asp Val Val
                420                 425                 430

Leu Val Ala Ile Asn Arg Asn Thr Gln Ser Ser Tyr Ser Ile Ser Gly
                435                 440                 445

Leu Gln Thr Ala Leu Pro Asn Gly Ser Tyr Ala Asp Tyr Leu Ser Gly
            450                 455                 460

Leu Leu Gly Gly Asn Gly Ile Ser Val Ser Asn Gly Ser Val Ala Ser
        465                 470                 475

Phe Thr Leu Ala Pro Gly Ala Val Ser Val Trp Gln Tyr Ser Thr Ser
480                 485                 490                 495

Ala Ser Ala Pro Gln Ile Gly Ser Val Ala Pro Asn Met Gly Ile Pro
                500                 505                 510

Gly Asn Val Val Thr Ile Asp Gly Lys Gly Phe Gly Thr Thr Gln Gly
                515                 520                 525

Thr Val Thr Phe Gly Gly Val Thr Ala Thr Val Lys Ser Trp Thr Ser
            530                 535                 540

Asn Arg Ile Glu Val Tyr Val Pro Asn Met Ala Ala Gly Leu Thr Asp
        545                 550                 555

Val Lys Val Thr Ala Gly Gly Val Ser Ser Asn Leu Tyr Ser Tyr Asn
560                 565                 570                 575

Ile Leu Ser Gly Thr Gln Thr Ser Val Val Phe Thr Val Lys Ser Ala
                580                 585                 590

Pro Pro Thr Asn Leu Gly Asp Lys Ile Tyr Leu Thr Gly Asn Ile Pro
            595                 600                 605

Glu Leu Gly Asn Trp Ser Thr Asp Thr Ser Gly Ala Val Asn Asn Ala
        610                 615                 620

Gln Gly Pro Leu Leu Ala Pro Asn Tyr Pro Asp Trp Phe Tyr Val Phe
    625                 630                 635

Ser Val Pro Ala Gly Lys Thr Ile Gln Phe Lys Phe Ile Lys Arg
640                 645                 650                 655

Ala Asp Gly Thr Ile Gln Trp Glu Asn Gly Ser Asn His Val Ala Thr
                660                 665                 670
```

```
Thr Pro Thr Gly Ala Thr Gly Asn Ile Thr Val Thr Trp Gln Asn
        675                 680                 685
```

<210> SEQ ID NO 3
<211> LENGTH: 39
<212> TYPE: DNA
<213> ORGANISM: Artificial Sequence
<220> FEATURE:
<223> OTHER INFORMATION: Mutagenisis Primer 1

<400> SEQUENCE: 3
ccgatcccgc gggattctca ttagcagatt tagatcagc          39

<210> SEQ ID NO 4
<211> LENGTH: 32
<212> TYPE: DNA
<213> ORGANISM: Artificial Sequence
<220> FEATURE:
<223> OTHER INFORMATION: Mutagenesis primer 2
<220> FEATURE:
<221> NAME/KEY: misc_feature
<222> LOCATION: (17)..(17)
<223> OTHER INFORMATION: n = a, t, c, or g

<400> SEQUENCE: 4
cccgcgggat cggtaanatt acggtaaatt cc          32

<210> SEQ ID NO 5
<211> LENGTH: 24
<212> TYPE: DNA
<213> ORGANISM: Artificial Sequence
<220> FEATURE:
<223> OTHER INFORMATION: Upstream Primer

<400> SEQUENCE: 5
tattataagg ggctccatta cctg          24

<210> SEQ ID NO 6
<211> LENGTH: 24
<212> TYPE: DNA
<213> ORGANISM: Artificial Sequence
<220> FEATURE:
<223> OTHER INFORMATION: Downstream Primer

<400> SEQUENCE: 6
cggatacttc agtttccaat gttg          24

<210> SEQ ID NO 7
<211> LENGTH: 18
<212> TYPE: DNA
<213> ORGANISM: Artificial Sequence
<220> FEATURE:
<223> OTHER INFORMATION: Primer 1

<400> SEQUENCE: 7
ksctatcayg ghtactgg          18

<210> SEQ ID NO 8
<211> LENGTH: 18
<212> TYPE: DNA
<213> ORGANISM: Primer 2

<400> SEQUENCE: 8
macrtcrttr ttkatcca          18

<210> SEQ ID NO 9

```
<211> LENGTH: 15
<212> TYPE: DNA
<213> ORGANISM: Artificial Sequence
<220> FEATURE:
<223> OTHER INFORMATION: Primer D3
<220> FEATURE:
<221> NAME/KEY: misc_feature
<222> LOCATION: (6)..(6)
<223> OTHER INFORMATION: n = a, t, c, g
<220> FEATURE:
<221> NAME/KEY: misc_feature
<222> LOCATION: (9)..(9)
<223> OTHER INFORMATION: n= a, t, c, or g
<220> FEATURE:
<221> NAME/KEY: misc_feature
<222> LOCATION: (12)..(12)
<223> OTHER INFORMATION: n= a, t, c, or g

<400> SEQUENCE: 9
gayccngcng gntty                                              15

<210> SEQ ID NO 10
<211> LENGTH: 15
<212> TYPE: DNA
<213> ORGANISM: Artificial Sequence
<220> FEATURE:
<223> OTHER INFORMATION: Primer D4
<220> FEATURE:
<221> NAME/KEY: misc_feature
<222> LOCATION: (4)..(4)
<223> OTHER INFORMATION: n = a, t,c, g
<220> FEATURE:
<221> NAME/KEY: misc_feature
<222> LOCATION: (7)..(7)
<223> OTHER INFORMATION: n = a, t,c, g
<220> FEATURE:
<221> NAME/KEY: misc_feature
<222> LOCATION: (10)..(10)
<223> OTHER INFORMATION: n = a, t,c, g

<400> SEQUENCE: 10
raanccngcn ggrtc                                              15

<210> SEQ ID NO 11
<211> LENGTH: 17
<212> TYPE: DNA
<213> ORGANISM: Artificial Sequence
<220> FEATURE:
<223> OTHER INFORMATION: Primer D5
<220> FEATURE:
<221> NAME/KEY: misc_feature
<222> LOCATION: (6)..(6)
<223> OTHER INFORMATION: n = a, t, c, g
<220> FEATURE:
<221> NAME/KEY: misc_feature
<222> LOCATION: (12)..(12)
<223> OTHER INFORMATION: n = a, t, c, g
<220> FEATURE:
<221> NAME/KEY: misc_feature
<222> LOCATION: (15)..(15)
<223> OTHER INFORMATION: n = a, t, c, g

<400> SEQUENCE: 11
ttyacngayc cngcngg                                            17

<210> SEQ ID NO 12
<211> LENGTH: 17
<212> TYPE: DNA
<213> ORGANISM: Artificial Sequence
<220> FEATURE:
<223> OTHER INFORMATION: Primer D6
<220> FEATURE:
<221> NAME/KEY: misc_feature
```

```
<222> LOCATION: (3)..(3)
<223> OTHER INFORMATION: n = a, c, t, g
<220> FEATURE:
<221> NAME/KEY: misc_feature
<222> LOCATION: (6)..(6)
<223> OTHER INFORMATION: n = a, c, t, g
<220> FEATURE:
<221> NAME/KEY: misc_feature
<222> LOCATION: (12)..(12)
<223> OTHER INFORMATION: n = a, c, t, g

<400> SEQUENCE: 12
ccngcnggrt cngtraa                                                    17

<210> SEQ ID NO 13
<211> LENGTH: 17
<212> TYPE: DNA
<213> ORGANISM: Artificial Sequence
<220> FEATURE:
<223> OTHER INFORMATION: Primer 7

<400> SEQUENCE: 13
ttcacggatc cagccgg                                                    17

<210> SEQ ID NO 14
<211> LENGTH: 17
<212> TYPE: DNA
<213> ORGANISM: Artificial Sequence
<220> FEATURE:
<223> OTHER INFORMATION: Primer 8

<400> SEQUENCE: 14
ccggctggat ccgtgaa                                                    17

<210> SEQ ID NO 15
<211> LENGTH: 58
<212> TYPE: DNA
<213> ORGANISM: Artificial Sequence
<220> FEATURE:
<223> OTHER INFORMATION: Novamyl 5' primer #9

<400> SEQUENCE: 15
gattacgcca agcttctaga tgcctgcagc agcagccgta agcagttccg caagcgtc      58

<210> SEQ ID NO 16
<211> LENGTH: 42
<212> TYPE: DNA
<213> ORGANISM: Artificial Sequence
<220> FEATURE:
<223> OTHER INFORMATION: Novamyl 3' primer #10

<400> SEQUENCE: 16
aacactaagc tttggacgcg tatccatttc tttgacgttc ca                        42

<210> SEQ ID NO 17
<211> LENGTH: 58
<212> TYPE: DNA
<213> ORGANISM: Artificial Sequence
<220> FEATURE:
<223> OTHER INFORMATION: CGTase 5' primer #11

<400> SEQUENCE: 17
gattacgcca agcttctaga tgcctgcagc agcagccgta gcaccggata cttcagtt      58

<210> SEQ ID NO 18
<211> LENGTH: 42
<212> TYPE: DNA
```

```
<213> ORGANISM: Artificial Sequence
<220> FEATURE:
<223> OTHER INFORMATION: CGTase 3' primer #12

<400> SEQUENCE: 18
aacactaagc tttggacgcg tagacaagtt gtagaagaag gt                              42

<210> SEQ ID NO 19
<211> LENGTH: 18
<212> TYPE: DNA
<213> ORGANISM: Artificial Sequence
<220> FEATURE:
<223> OTHER INFORMATION: General 5' primer #13

<400> SEQUENCE: 19
gattacgcca agcttcta                                                        18

<210> SEQ ID NO 20
<211> LENGTH: 21
<212> TYPE: DNA
<213> ORGANISM: Artificial Sequence
<220> FEATURE:
<223> OTHER INFORMATION: General 3' primer # 14

<400> SEQUENCE: 20
aacactaagc tttggacgcg t                                                    21

<210> SEQ ID NO 21
<211> LENGTH: 36
<212> TYPE: DNA
<213> ORGANISM: Artificial Sequence
<220> FEATURE:
<223> OTHER INFORMATION: Mutasgenesis primer 1

<400> SEQUENCE: 21
cttgtacgat cttgcagatc tgtcgcagga aaatgg                                    36

<210> SEQ ID NO 22
<211> LENGTH: 41
<212> TYPE: DNA
<213> ORGANISM: Artificial Sequence
<220> FEATURE:
<223> OTHER INFORMATION: Mutagenesis primer 2

<400> SEQUENCE: 22
gacagatctg caagatcgta caagtttctt cattgcgcct c                              41

<210> SEQ ID NO 23
<211> LENGTH: 20
<212> TYPE: DNA
<213> ORGANISM: Artificial Sequence
<220> FEATURE:
<223> OTHER INFORMATION: A82 Oligomer

<400> SEQUENCE: 23
ggggatctgg aggggttcg                                                       20

<210> SEQ ID NO 24
<211> LENGTH: 22
<212> TYPE: DNA
<213> ORGANISM: Artificial Sequence
<220> FEATURE:
<223> OTHER INFORMATION: B346 oligomer

<400> SEQUENCE: 24
tttgtactcg ttccccgttt gg                                                   22
```

```
<210> SEQ ID NO 25
<211> LENGTH: 42
<212> TYPE: DNA
<213> ORGANISM: Artificial Sequence
<220> FEATURE:
<223> OTHER INFORMATION: Primer A90

<400> SEQUENCE: 25
ggttggcagt cccgggatcg tctccaaacc actcgccaaa tg                42

<210> SEQ ID NO 26
<211> LENGTH: 41
<212> TYPE: DNA
<213> ORGANISM: Artificial Sequence
<220> FEATURE:
<223> OTHER INFORMATION: Primer A91

<400> SEQUENCE: 26
gatcccggga ctgccaacca tgtaaataat acgtattttg c                 41

<210> SEQ ID NO 27
<211> LENGTH: 5
<212> TYPE: PRT
<213> ORGANISM: Artificial Sequence
<220> FEATURE:
<223> OTHER INFORMATION: Variation

<400> SEQUENCE: 27

Asp Pro Ala Gly Phe
1               5

<210> SEQ ID NO 28
<211> LENGTH: 4
<212> TYPE: PRT
<213> ORGANISM: Artificial Sequence
<220> FEATURE:
<223> OTHER INFORMATION: Variation

<400> SEQUENCE: 28

Asp Ala Gly Phe
1

<210> SEQ ID NO 29
<211> LENGTH: 4
<212> TYPE: PRT
<213> ORGANISM: Artificial Sequence
<220> FEATURE:
<223> OTHER INFORMATION: Variation

<400> SEQUENCE: 29

Asp Pro Gly Phe
1

<210> SEQ ID NO 30
<211> LENGTH: 6
<212> TYPE: PRT
<213> ORGANISM: Artificial Sequence
<220> FEATURE:
<223> OTHER INFORMATION: Variation

<400> SEQUENCE: 30

Asp Pro Ala Ala Gly Phe
1               5

<210> SEQ ID NO 31
```

-continued

```
<211> LENGTH: 7
<212> TYPE: PRT
<213> ORGANISM: Artificial Sequence
<220> FEATURE:
<223> OTHER INFORMATION: Variation

<400> SEQUENCE: 31

Asp Pro Ala Ala Gly Gly Phe
1               5
```